(12) United States Patent
Amin et al.

(10) Patent No.: US 6,313,136 B1
(45) Date of Patent: Nov. 6, 2001

(54) IMIDAZO PYRIDINE DERIVATIVES WHICH INHIBIT GASTRIC ACID SECRETION

(75) Inventors: Kosrat Amin; Mikael Dahlström, both of Mölndal; Peter Nordberg, Sävedalen; Ingemar Starke, Göteborg, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/319,890

(22) PCT Filed: Apr. 23, 1999

(86) PCT No.: PCT/SE99/00662

§ 371 Date: Jun. 14, 1999

§ 102(e) Date: Jun. 14, 1999

(87) PCT Pub. No.: WO99/55705

PCT Pub. Date: Nov. 4, 1999

(30) Foreign Application Priority Data

Apr. 29, 1998 (SE) .................................................. 9801526

(51) Int. Cl.⁷ ........................ A61K 31/435; C07D 471/04
(52) U.S. Cl. ...................... 514/300; 514/233.2; 514/253; 546/121; 544/127; 544/362
(58) Field of Search ............................ 546/121; 544/127, 544/362; 514/300, 233.2, 253

(56) References Cited

U.S. PATENT DOCUMENTS

| | | | |
|---|---|---|---|
| 4,450,164 | * 5/1984 | Bristol et al. ........................ | 546/121 |
| 4,725,601 | * 2/1988 | Ueda et al. ........................... | 514/300 |
| 4,920,129 | * 4/1990 | Shiokowa et al. .................... | 514/300 |

FOREIGN PATENT DOCUMENTS

| | | |
|---|---|---|
| 0033094 | * 5/1981 | (EP) . |
| 0204285 | * 12/1986 | (EP) . |
| 0228006 | * 7/1987 | (EP) . |
| 0308917 | * 3/1989 | (EP) . |

OTHER PUBLICATIONS

Kaminski, et al., J. Med. Chem. 28, 876–892 (1985).*
Kaminski, et al., J. Med. Chem. 30, 2031–2046 (1987).*
Kaminski, et al., J.Med. Chem. 30, 2047–2051 (1987).*
Kaminski, et al., J.Med. Chem. 32, 1686–1700 (1989).*
Kaminski, et al., J.Med. Chem. 34, 533–541 (1991).*

* cited by examiner

Primary Examiner—Bernard Dentz
(74) Attorney, Agent, or Firm—White & Case LLP

(57) ABSTRACT

The present invention relates to imidazo pyridine derivatives of the formula (I), in which the phenyl moiety is substituted, and in which the imidazo pyridine moiety is substituted with a carboxamide group in 6-position, which inhibit exogenously or endogenously stimulated gastric acid secretion and thus can be used in the prevention and treatment of gastrointestinal inflammatory diseases.

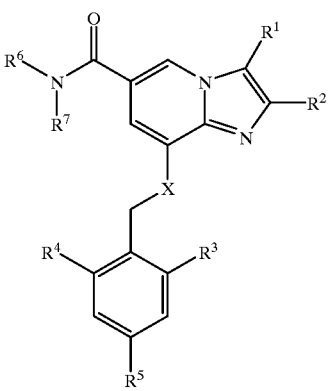

44 Claims, No Drawings

IMIDAZO PYRIDINE DERIVATIVES WHICH INHIBIT GASTRIC ACID SECRETION

This application is a 371 of PCT/SE99/00662 filed Apr. 23, 1999.

TECHNICAL FIELD

The present invention relates to novel compounds, and pharmaceutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a pharmaceutically acceptable salt thereof, as active ingredient; and to the use of the active compounds in the manufacture of medicaments for the medical use indicated above. The invention also relates to new intermediates for in the preparation of the novel compounds.

BACKGROUND ART

Substituted imidazo[1,2-a]pyridines, useful in the treatment of peptic ulcer diseases, are known in the art, e.g. from EP-B-0033094 and U.S. Pat. No. 4,450,164 (Schering Corporation); from EP-B-0204285 and U.S. Pat. No. 4,725,601 (Fujisawa Pharmaceutical Co.); and from publications by J. J. Kaminski et al. in the Journal of Medical Chemistry (vol. 28, 876–892, 1985; vol. 30, 2031–2046, 1987; vol. 30, 2047–2051, 1987; vol. 32, 1686–1700, 1989; and vol. 34, 533–541, 1991).

For a review of the pharmacology of the gastric acid pump (the $H^+$, $K^+$-ATPase), see Sachs et al. (1995) Annu. Rev. Pharmacol. Toxicol. 35: 277–305.

DISCLOSURE OF THE INVENTION

It has surprisingly been found that compounds of the Formula I, which are imidazo pyridine derivatives in which the phenyl moiety is substituted, and in which the imidazo pyridine moiety is substituted with a carboxamide group in 6-position are particularly effective as inhibitors of the gastrointestinal $H^+$, $K^+$-ATPase and thereby as inhibitors of gastric acid secretion. The carboxamide group in 6-position is optionally selected to give compounds of Formula I a molecular weight $\leq 600$.

In one aspect, the invention thus relates to compounds of the general Formula I

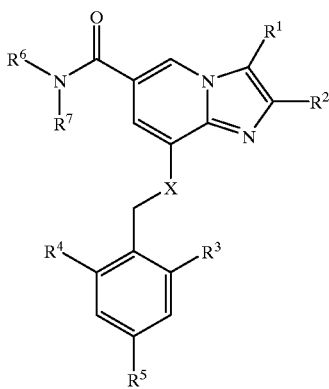

I or a pharmaceutically acceptable salt thereof, wherein
$R^1$ is
  (a) H,
  (b) $CH_3$, or
  (c) $CH_2OH$;
$R^2$ is
  (a) $CH_3$, or
  (b) $CH_2CH_3$;
$R^3$ is
  (a) H,
  (b) $C_1$–$C_6$ alkyl,
  (c) hydroxylated $C_1$–$C_6$ alkyl, or
  (d) halogen;
$R^4$ is
  (a) H,
  (b) $C_1$–$C_6$ alkyl,
  (c) hydroxylated $C_1$–$C_6$ alkyl, or
  (d) halogen;
$R^5$ is
  (a) H, or
  (b) halogen;
$R^6$ and $R^7$ are independently selected substituents, comprising C, H, N, O, S, Se, P and Halogen atoms, which give compounds of Formula I a molecular weight $\leq 600$, provided that at least one of $R^6$ and $R^7$ can not be H, $C_1$–$C_6$ alkyl, hydroxylated $C_1$–$C_6$ alkyl, or $C_1$–$C_6$ alkoxy-substituted $C_1$–$C_6$ alkyl, and
X is
  (a) NH, or
  (b) O.

As used herein, the term "$C_1$–$C_6$ alkyl" denotes a straight or branched alkyl group having from 1 to 6 carbon atoms. Examples of said $C_1$–$C_6$ alkyl include methyl, ethyl, n-propyl, iso-propyl, n-butyl, iso-butyl, sec-butyl, t-butyl and straight- and branched-chain pentyl and hexyl.

The term "halogen" includes fluoro, chloro, bromo and iodo.

The substitutents $R^6$ and $R^7$ are defined as independently selected substituents, comprising C, H, N, O, S, Se, P or Halogen atoms, which give compounds of Formula I a molecular weight $\leq 600$, which is a definition easily understood by a person skilled in the art.

Examples of substituents that fall within the scope of this definition includes, but is not limited to,
  (a) H,
  (b) $C_1$–$C_6$ alkyl,
  (c) hydroxylated $C_1$–$C_6$ alkyl,
  (d) $C_1$–$C_6$ alkoxy-substituted $C_1$–$C_6$ alkyl,
  (e) $C_2$–$C_6$ alkenyl,
  (f) $C_2$–$C_6$ alkynyl,
  (g) halogenated $C_1$–$C_6$ alkyl,
  (h) $C_3$–$C_8$ cycloalkyl,
  (i) cycloalkyl-substituted $C_1$–$C_6$ alkyl,
  (j) aryl, in which aryl represents phenyl, pyridyl, thienyl, imidazolyl, indolyl, naphthyl or furanyl, optionally substituted by one or more substituents selected from halogen, $C_1$–$C_6$ alkyl, $C_1$–$C_6$ alkoxy, $CF_3$, OH, nitro, amino, $C_1$–$C_6$ alkyl-NH—, ($C_1$–$C_6$ alkyl)$_2$—N—, or CN or $NH_2SO_2$,
  (k) aryl substituted $C_1$–$C_6$ alkyl, in which aryl represents phenyl, pyridyl, thienyl, imidazolyl, indolyl, naphthyl or furanyl, optionally substituted with one or more substituents selected from halogen, $C_1$–$C_6$ alkyl, $C_1$–$C_6$ alkoxy, $CF_3$, OH, nitro, amino $C_1$–$C_6$ alkyl-NH—, ($C_1$–$C_6$ alkyl)$_2$—N—, CN or $NH_2SO_2$,
  (l) $R^8$—($C_1$–$C_6$) alkyl-, wherein $R^8$ is $NH_2C=O$—, $C_1$–$C_6$ alkyl-NHC=O—, ($C_1$–$C_6$ alkyl)$_2$NC=O—, $C_1$–$C_6$ alkyl-OOC—, $NH_2SO_2$—, $C_1$–$C_6$ alkyl-$SO_2NH$—, $ArSO_2NH$—, cyano, $C_1$–$C_6$ alkyl-CO—NH—, $C_1$–$C_6$ alkyl-OOCNH—, $C_1$–$C_6$ alkyl-O—, $C_7$–$C_{12}$ alkyl-O—$C_1$–$C_6$ alkyl-SO—, $C_1$–$C_6$ alkyl-S—, $C_1$–$C_6$ alkyl-$SO_2$—, $C_1$–$C_6$ alkyl-C=O—, $NH_2$—, $C_1$–$C_6$ alkyl-NH—, ($C_1$–$C_6$ alkyl)$_2$N—, ArCONH—, Ar($C_1$–$C_6$ alkyl)CONH, $ArNHSO_2$—, (Ar)$_2$—N—$SO_2$—, $C_1$–$C_6$ alkyl-$NHSO_2$—, ArS—, ArSO—, $ArSO_2$—, ArC=O—, $NH_2CONH$—$C_1$–$C_6$ alkyl-NHCONH—, ($C_1$–$C_6$ alkyl)$_2$—NCONH—, ArNHCONH—, Ar—O—, Ar—NH—, Ar($C_1$–$C_6$ alkyl)N—, ($C_1$–$C_6$ alkyl)$_2$$NSO_2$—, hydroxylated C1–C6 alkyl-O— or morpholinyl; wherein Ar represents phenyl, pyridyl, thienyl, imidazolyl, indolyl, naphthyl or furanyl, optionally substituted with one or more substituents selected from halogen, $C_1$–$C_6$ alkyl, $C_1$–$C_6$ alkoxy, $CF_3$, OH, CN, nitro, amino, $C_1$–$C_6$ alkyl-NH—, or ($C_1$–$C_6$ alkyl)$_2$N—, (m) $C_7$–$C_{12}$, (n) OH, O—$C_1$–$C_6$ alkyl, or O-hydroxylated $C_1$–$C_6$ alkyl, o)

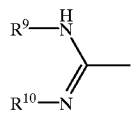

wherein $R^9$ and $R^{10}$ are independently H or $C_1$–$C_6$ alkyl, p) $R^{11}$—($C_1$–$C_6$) alkyl-COO—($C_1$–$C_6$) alkyl- wherein $R^{11}$ is HOOC—, $C_1$–$C_6$ alkyl-OOC— or an amino carbonyl group with the formula

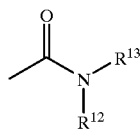

wherein $R^{12}$, $R^{13}$ are the same or different H, or $C_1$–$C_6$ alkyl $R^6$ and $R^7$, together with the nitrogen atom to which they are attached, form a saturated or unsaturated ring optionally containing one or more further heteroatoms (for example morpholine, piperazine, pyrrolidine, piperidine), optionally substituted with one or more substituents selected from halogen, $C_1$–$C_6$ alkyl, $C_1$–$C_6$ alkoxy, $CF_3$, OH, nitro, amino $C_1$–$C_6$ alkyl-NH—, ($C_1$–$C_6$ alkyl)$_2$—N—, CN, $NH_2SO_2$, phenyl, $NH_2CO$—, $C_1$–$C_6$ alkyl-CO—, the ring can be fused with an aromatic ring (such as tetrahydroquinoline);

Both the pure enantiomers, racemic mixtures and unequal mixtures of two enantiomers are within the scope of the invention. It should be understood that all the diastereomeric forms possible (pure enantiomers, racemic mixtures and unequal mixtures of two enantiomers) are within the scope of the invention. Also included in the invention are derivatives of the compounds of the Formula I which have the biological function of the compounds of the Formula I, such as prodrugs.

It will also be appreciated by those skilled in the art, although derivatives of compounds of formula I may not possess pharmacological activity as such, they may be administered parenterally or orally and thereafter metabolised in the body to form compounds of the invention which are pharmacologically active. Such derivatives may therefore be described as "prodrugs". All prodrugs of compounds of formula I are included within the scope of the invention.

Depending on the process conditions the end products of the Formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrohalogen acids such as hydrochloric acid, sulphuric acid, phosphoric acid, nitric acid, aliphatic, alicyclic, aromatic or heterocyclic carboxyl or sulphonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulphonic acid, ethanesulphonic acid, hydroxyethanesulphonic acid, halogenbensenesulphonic acid, toluenesulphonic acid or naphthalenesulphonic acid.

Preferred compounds according to the invention are those of the Formula I wherein $R^1$ is $CH_3$ or $CH_2OH$; $R^2$ is $CH_3$ or $CH_2CH_3$; $R^3$ is $CH_3$ or $CH_2CH_3$; $R^4$ is $CH_3$ or $CH_2CH_3$; $R^5$ is H, Br, Cl, or F; $R^6$ and $R^7$ are independently (provided that at least one of $R^6$ and $R^7$ can not be H, $C_1$–$C_6$ alkyl, hydroxylated $C_1$–$C_6$ alkyl or $C_1$–$C_6$ alkoxy-substituted $C_1$–$C_6$ alkyl):

(a) H, (b) $C_1$–$C_6$ alkyl, (c) hydroxylated $C_1$–$C_6$ alkyl, (d) $C_1$–$C_6$ alkoxy-substituted $C_1$–$C_6$ alkyl, (e) $C_2$–$C_6$ alkenyl, (f) $C_2$–$C_6$ alkynyl, (g) halogenated $C_1$–$C_6$ alkyl, (h) $C_3$–$C_8$ cycloalkyl, (i) cycloalkyl-substituted $C_1$–$C_6$ alkyl, (j) aryl, in which aryl represents phenyl, pyridyl, thienyl, imidazolyl, indolyl, naphthyl or furanyl, optionally substituted by one or more substituents selected from halogen, $C_1$–$C_6$ alkyl, $C_1$–$C_6$ alkoxy, $CF_3$, OH, nitro, amino, $C_1$–$C_6$ alkyl-NH—, ($C_1$–$C_6$ alkyl)$_2$—N—, or CN or $NH_2SO_2$, (k) aryl substituted $C_1$–$C_6$ alkyl, in which aryl represents phenyl, pyridyl, thienyl, imidazolyl, indolyl, naphthyl or furanyl, optionally substituted with one or more substituents selected from halogen, $C_1$–$C_6$ alkyl, $C_1$–$C_6$ alkoxy, $CF_3$, OH, nitro, amino $C_1$–$C_6$ alkyl-NH—, ($C_1$–$C_6$ alkyl)$_2$—N—, CN or $NH_2SO_2$, (l) $R^8$—($C_1$–$C_6$) alkyl-, wherein $R^8$ is $NH_2C$=O—, $C_1$–$C_6$ alkyl-NHC=O—, ($C_1$–$C_6$ alkyl)$_2$NC=O—, $C_1$–$C_6$ alkyl-OOC—, $NH_2SO_2$—, $C_1$–$C_6$ alkyl-$SO_2NH$—, $ArSO_2NH$—, cyano, $C_1$–$C_6$ alkyl-CO—NH—, $C_1$–$C_6$ alkyl-OOCNH—, $C_1$–$C_6$ alkyl-O—, $C_7$–$C_{12}$ alkyl-O—$C_1$–$C_6$ alkyl-SO—, $C_1$–$C_6$ alkyl-S—, $C_1$–$C_6$ alkyl-$SO_2$—, $C_1$–$C_6$ alkyl-C=O—, $NH_2$—, $C_1$–$C_6$ alkyl-NH—, ($C_1$–$C_6$ alkyl)$_2$N—, ArCONH—, Ar($C_1$–$C_6$ alkyl)CONH, $ArNHSO_2$—, (Ar)$_2$—N—$SO_2$—, $C_1$–$C_6$ alkyl-$NHSO_2$—, ArS—, ArSO—, $ArSO_2$—, ArC=O—, $NH_2CONH$—$C_1$–$C_6$ alkyl)$_2$—NCONH—, ArNHCONH—, ($C_1$–$C_6$ alkyl)$_2$—N—$SO_2$—, Ar—O—, Ar—NH—, Ar($C_1$–$C_6$ alkyl)N—, ($C_1$–$C_6$ alkyl)$_2$$NSO_2$—, hydroxylated $C_1$–$C_6$ alkyl-O- or morpholinyl; wherein Ar represents phenyl, pyridyl, thienyl, imidazolyl, indolyl, naphthyl or furanyl, optionally substituted with one or more substituents selected from halogen, $C_1$–$C_6$ alkyl, $C_1$–$C_6$ alkoxy, $CF_3$, OH, CN, nitro, amino, $C_1$–$C_6$ alkyl-NH—, or ($C_1$–$C_6$ alkyl)$_2$N—, (m) $C_7$–$C_{12}$ alkyl, (n) OH, O—$C_1$–$C_6$ alkyl, or O-hydroxylated $C_1$–$C_6$ alkyl, (o)

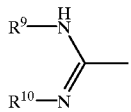

wherein $R^9$ and $R^{10}$ are independently H or $C_1$–$C_6$ alkyl, (p) $R^{11}$—($C_1$–$C_6$) alkyl-COO—($C_1$–$C_6$) alkyl- wherein $R^{11}$ is HOOC—, $C_1$–$C_6$ alkyl-OOC— or an amino carbonyl group with the formula

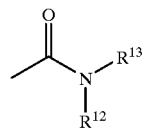

wherein $R^{12}$, $R^{13}$ are the same or different H, or $C_1$–$C_6$ alkyl $R^6$ and $R^7$, together with the nitrogen atom to which they are attached, form a saturated or unsaturated ring optionally containing one or more further heteroatoms (for example morpholine, piperazine, pyrrolidine, piperidine), optionally substituted with one or more substituents selected from halogen, $C_1$–$C_6$ alkyl, $C_1$–$C_6$ alkoxy, $CF_3$, OH, nitro, amino $C_1$–$C_6$ alkyl-NH—, ($C_1$–$C_6$ alkyl)$_2$—N—, CN, $NH_2SO_2$, phenyl, $NH_2CO$—, $C_1$–$C_6$ alkyl-CO—, the ring can be fused with an aromatic ring (such as tetrahydroquinoline);

More preferred compounds according to the invention are those of the Formula I wherein $R^1$ is $CH_3$ or $CH_2OH$; $R^2$ is $CH_3$, $R^3$ is $CH_3$ or $CH_2CH_3$; $R^4$ is $CH_3$ or $CH_2CH_3$; $R^5$ is H, Br, Cl, or F; $R^6$ and $R^7$ are independently (provided that at least one of $R^6$ and $R^7$ can not be H, $C_1$–$C_6$ alkyl, hydroxylated $C_1$–$C_6$ alkyl or $C_1$–$C_6$ alkoxy-substituted $C_1$–$C_6$ alkyl):

(a) H, (b) $C_1$–$C_6$ alkyl, (c) hydroxylated $C_1$–$C_6$ alkyl, (d) $C_1$–$C_6$ alkoxy-substituted $C_1$–$C_6$ alkyl, (e) halogenated $C_1$–$C_6$ alkyl, (f) aryl, in which aryl represents phenyl, pyridyl, imidazolyl, indolyl, or naphthyl, optionally substituted by one or more substituents selected from halogen, $C_1$–$C_6$ alkyl, $C_1$–$C_6$ alkoxy, $CF_3$, OH, $C_1$–$C_6$ alkyl-NH—, ($C_1$–$C_6$ alkyl)$_2$—N—, or CN—, (g) aryl substituted $C_1$–$C_6$ alkyl, in which aryl represents phenyl, pyridyl, imidazolyl, indolyl, or naphthyl, optionally substituted with one or more substituents selected from halogen, $C_1$–$C_6$ alkyl, $C_1$–$C_6$ alkoxy, $CF_3$, or OH, (h) $R^8$—($C_1$–$C_6$) alkyl-, wherein $R^8$ is $NH_2C$=O—, $C_1$–$C_6$ alkyl-NHC=O—, ($C_1$–$C_6$ alkyl)$_2$NC=O—, $C_1$–$C_6$ alkyl-OOC—, cyano, $C_1$–$C_6$ alkyl-CO—NH—, $C_1$–$C_6$ alkyl-OOCNH—, $C_1$–$C_6$ alkyl-O—, $C_7$–$C_{12}$ alkyl-O—$C_1$–$C_6$ alkyl-SO—, $C_1$–$C_6$ alkyl-S—, $C_1$–$C_6$ alkyl-C=O—, —ArCONH—, Ar($C_1$–$C_6$ alkyl)CONH, ArC=O—, $NH_2CONH$—$C_1$–$C_6$ alkyl-NHCONH—, ($C_1$–$C_6$ alkyl)$_2$—NCONH—, ArNHCONH—, hydroxylated C1–C6 alkyl-O— or morpholinyl; wherein Ar represents phenyl, pyridyl, imidazolyl, indolyl, or naphthyl optionally substituted with one or more substituents selected from halogen, $C_1$–$C_6$ alkyl, $C_1$–$C_6$ alkoxy, $CF_3$, OH, CN, (i) $C_7$–$C_{12}$ alkyl, (j) OH, (k) $R^{11}$—($C_1$–$C_6$) alkyl-COO—($C_1$–$C_6$) alkyl- wherein $R^{11}$ is HOOC—, or $C_1$–$C_6$ alkyl-OOC $R^6$ and $R^7$, together with the nitrogen atom to which they are attached, form a saturated or unsaturated ring optionally containing one or more further heteroatoms (for example morpholine, piperazine, pyrrolidine, piperidine), optionally substituted with one or more substituents selected from halogen, $C_1$–$C_6$ alkyl, $C_1$–$C_6$ alkoxy, $CF_3$, OH, nitro, amino, CN, $NH_2SO_2$, phenyl, $NH_2CO$—, $C_1$–$C_6$ alkyl-CO—, the ring can be fused with an aromatic ring (such as tetrahydroquinoline)

Most preferred compounds according to the invention are;

2,3-dimethyl-8-(2-ethyl-6-methylbenzylamino)-6-(morpholinocarbonyl)-imidazo[1,2-a]pyridine N-(4-ethoxyphenyl)-8-(2-ethyl-6-methylbenzylamino)-2,3-dimethylimidazo[1,2-a]pyridine-6-carboxamide N-[2-(dimethylamine)-2-oxoethyl]-8-(2-ethyl-6-methylbenzylamino)-N,2,3-trimethylimidazo[1,2-a]pyridine-6-carboxamide (8-(2-ethyl-6-methylbenzylamino)-2,3-dimethylimidazo[1,2-a]pyridin-yl)(4-methylpiperazino)methanone 1-((8-(2-ethyl-6-methylbenzylamino)-2,3-dimethylimidazo[1,2-a]pyridin-6-yl)carbonyl)-2-(s)-pyrrolidinecarboxamide 8-(2-ethyl-6-methylbenzylamino)-N-hydroxy-2,3-dimethylimidazo[1,2-a]pyridine-6-carboxamide (2-ethyl-6methylbenzylamino)-N-(2-(2-hydroxyethoxy)ethyl)-2,3-dimethylimidazo[1,2-a]pyridine-6-carboxamide (8-(2-ethyl-6-methylbenzylamino)-2,3-dimethylimidazo[1,2-a]pyridin-6-yl)(3-hydroxy-1-pyrrolidinyl)methanone N-(3,4-dihydroxyphenethyl)-8-(2-ethyl-6-methylbenzylamino)-2,3-dimethylimidazo[1,2-a]pyridine-6-carboxamide 8-(2-ethyl-6-methylbenzylamino-3-(hydroxymethyl)-2-methyl-6-(morpholinocarbonyl)imidazo[1,2-a]pyridine N-((8-(2-ethyl-6-methylbenzyl)amino)-2,3-dimethylimidazo[1,2-a]pyridin-6-yl)carbonyl)guanidine 4-(2-(((8-(2-ethyl-6-methylbenzylamino)-2,3-dimethylimidazo[1,2-a]pyridin-6-yl)carbonyl)amino)ethoxy)-4-oxobutanoic acid Preparation The present invention also provides the following process for the manufacture of compounds with the general Formula I.

A process for manufacture of compounds with the general Formula I comprises the following steps:

a) Compounds of Formula II

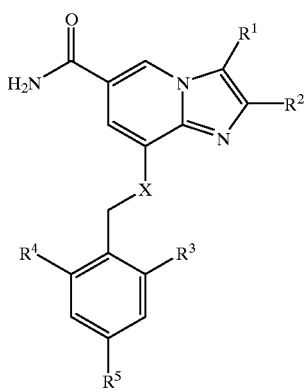

wherein $R^1$, $R^2$, $R^3$, $R^4$, $R^5$, and X are as defined in Formula I, can be hydrolyzed under standard conditions to the corresponding carboxylic acid compounds of Formula III

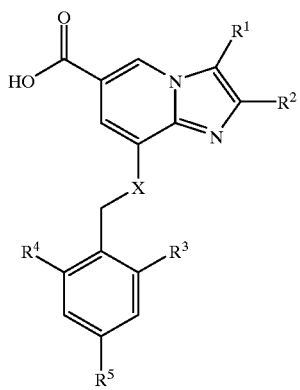

b) Compounds of the Formula III wherein $R^1$, $R^2$, $R^3$, $R^4$, $R^5$ and X is as defined in Formula I can be reacted with amino compounds of Formula IV

wherein $R^6$ and $R^7$ are as defined for Formula I, in the presence of a coupling reagent to the corresponding amide compounds of the Formula I. The reaction can be carried out in an inert solvent under standard conditions.

The present invention also provides the following process for the manufacture of intermediate compounds with the general Formula II.

A process for manufacture of compounds with the general Formula II wherein X is NH comprises the following steps:

a) Compounds of the general Formula V

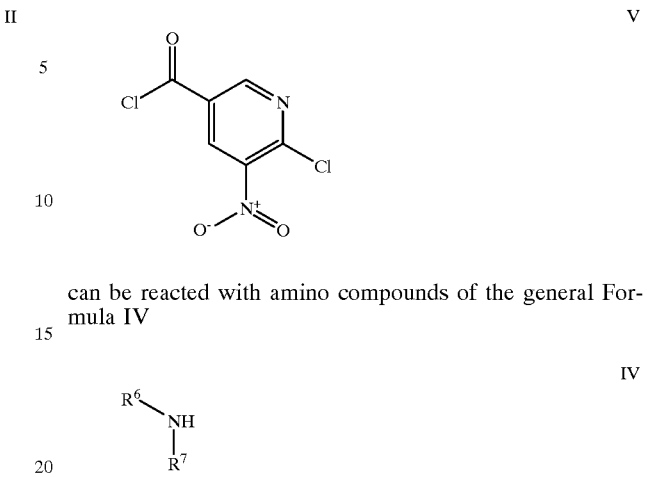

can be reacted with amino compounds of the general Formula IV

wherein $R^6$ and $R^7$ are both hydrogen, to the corresponding amide of the Formula VI. The reaction can be carried out in standard conditions in an inert solvent.

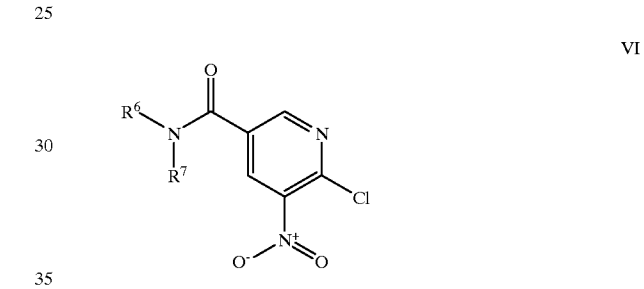

b) Compounds of the general Formula VI can be reacted with ammonia to compounds of the general Formula VII

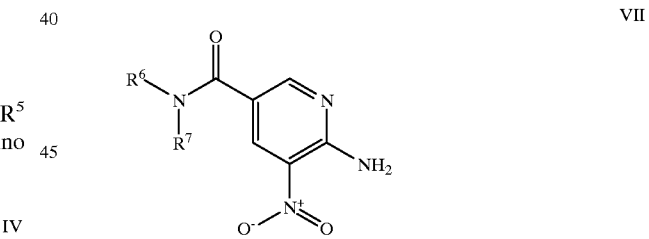

wherein $R^6$ and $R^7$ are both hydrogen. The reactions can be carried out under standard conditions in an inert solvent.

c) Compounds of the Formula VII can be reduced e.g. by using hydrogen and a catalyst such as Pd/C to compounds of the Formula VIII

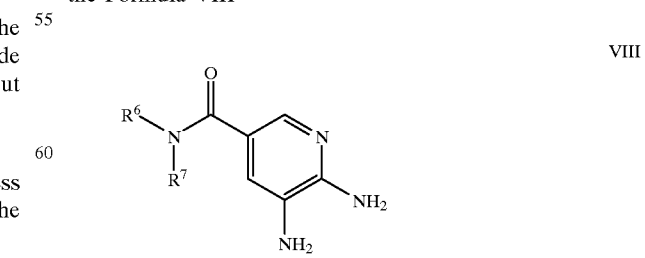

wherein $R^6$ and $R^7$ are both hydrogen. The reaction can be carried out under standard conditions in an inert solvent.

d) The imidazo[1,2-a]pyridine compounds of the Formula X can be prepared by reacting compounds of the general Formula VIII with compounds of the general Formula IX

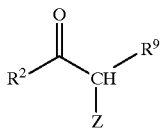

IX wherein $R^2$ is as defined for Formula I and Z is a leaving group such as halogen, mesyl, tosyl and $R^9$ represents H, $CH_3$ or an ester group such as $COOCH_3$, $COOC_2H_5$ etc.

The reaction is carried out under standard conditions in an inert solvent such as acetone, acetonitrile, alcohol, dimethylformamide, etc. with or without a base.

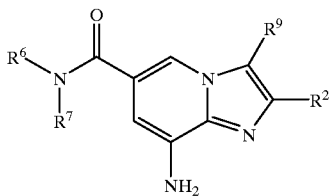

X e) Compounds of the Formula X can be reacted with compounds of the Formula XI

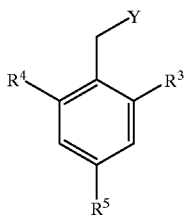

XI wherein $R^3$, $R^4$ and $R^5$ are as defined for Formula I and Y is a leaving group, such as a halide, tosyl or mesyl, to the compounds of the Formula XII.

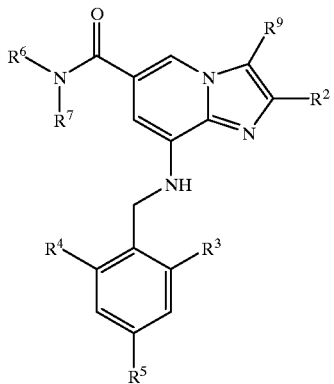

XII wherein $R^2$, $R^3$, $R^4$, and $R^5$ are as defined for Formula I and $R^6$ and $R^7$ both hydrogen and $R_9$ is H, $CH_3$ or an ester group such as $COOCH_3$, $COOC_2H_5$, etc. It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide, an alkali metal carbonate, such as potassium carbonate and sodium carbonate; or an organic amine, such as triethylamine.

f) Reduction of compounds of the general Formula XII wherein $R^9$ is an ester group e.g. by using lithium borohydride in an inert solvent, such as tetrahydrofuran or diethyl ether, to the compounds of the general Formula I wherein $R^1$ is $CH_2OH$ and R6 and R7 are both hydrogen.

Medical Use

In a further aspect, the invention relates to compounds of the formula I for use in therapy, in particular for use against gastrointestinal inflammatory diseases. The invention also provides the use of a compound of the formula I in the manufacture of a medicament for the inhibition of gastric acid secretion, or for the treatment of gastrointestinal inflammatory diseases.

The compounds according to the invention may thus be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrome. Furthermore, the compounds may be used for treatment of other gastrointestinal disorders where gastric antisecretory effect is desirable, e.g. in patients with gastrinomas, and in patients with acute upper gastrointestinal bleeding. They may also be used in patients in intensive care situations, and pre- and postoperatively to prevent acid aspiration and stress ulceration.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

Pharmaceutical Formulations

In yet a further aspect, the invention relates to pharmaceutical compositions containing at least one compound of the invention, or a pharmaceutically acceptable salt thereof, as active ingredient.

The compounds of the invention can also be used in formulations together with other active ingredients, e.g. antibiotics such as amoxicillin.

For clinical use, the compounds of the invention are formulated into pharmaceutical formulations for oral, rectal, parenteral or other mode of administration. The pharmaceutical formulation contains at least one compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention, vegetable oil, fat, or other suitable vehicle for soft gelatin capsules. Hard gelatin capsules may contain granules of the active compound. Hard gelatin capsules may also contain the active compound in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

The compounds according to the present invention can also be used in formulations, together or in combination for simultaneous, separate or sequential use, with other active ingredients, e.g. for the treatment or prophylaxis of conditions involving infection by *Helicobacter pylori* of human gastric mucosa. Such other active ingredients may be antimicrobial agents, in particular:

β-lactam antibiotics such as amoxicillin, ampicillin, cephalothin, cefaclor or cefixime;

macrolides such as erythromycin, or clarithromycin;

tetracyclines such as tetracycline or doxycycline;

aminoglycosides such as gentamycin, kanamycin or amikacin;

quinolones such as norfloxacin, ciprofloxacin or enoxacin;

others such as metronidazole, nitrofurantoin or chloramphenicol; or preparations containing bismuth salts such as bismuth subcitrate, bismuth subsalicylate, bismuth subcarbonate, bismuth subnitrate or bismuth subgallate.

The compounds according to the present invention can also be used together or in combination for simultaneous, separate or sequential use with antacids such as aluminium hydroxide, magnesium carbonate and magnesium hydroxid or alginic acid, or together or in combination for simultaneous, separate or sequential use with pharmaceuticals which inhibit acid secretion, such as, H2-blockers (e.g cimetidine, ranitidine), $H^+/K^+$-ATPase inhibitors (e.g. omeprazole, pantoprazole, lansoprazole or rabeprazole), or together or in combination for simultaneous, separate or sequential use with gastroprokinetics (e.g. cisapride or mosapride).

Intermediates

A further aspect of the invention is new intermediate compounds which are useful in the synthesis of compounds according to the invention.

Thus, the invention includes (a) a compound of the formula III

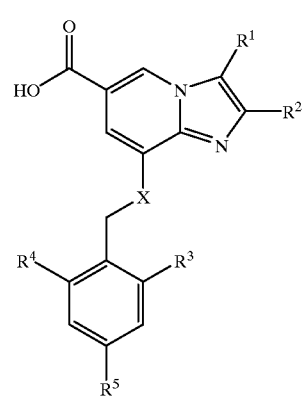

III wherein $R^1$, $R^2$, $R^3$, $R^4$, $R^5$ and X are as defined for Formula I;

(b) a compound of the formula X

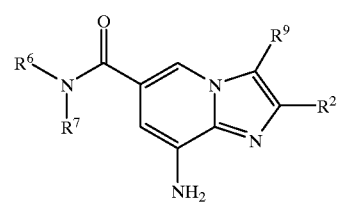

X wherein $R^2$, $R^6$ and $R^7$ are as defined for Formula I, and $R^9$ is H, $CH_3$ or an ester group such as $COOCH_3$, $COOC_2H_5$, etc.;

(c) a compound of the formula XII

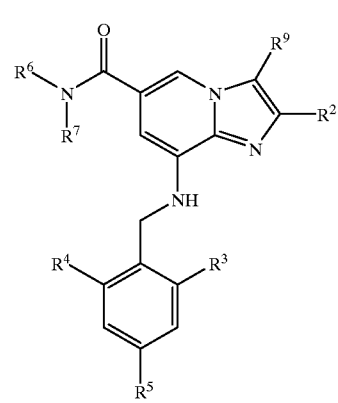

XII wherein $R^2$, $R^3$, $R^4$, $R^5$, $R^6$ and $R^7$ are as defined for Formula I, and $R^9$ is an ester group such as $COOCH_3$, $COOC_2H_5$ etc.

EXAMPLES

1. Preparation of Compounds of the Invention

Example 1.1

Synthesis of 2,3-dimethyl-8-(2-ethyl-6-methylbenzylamino)-6-(morpholinocarbonyl)-imidazo[1,2-a]pyridine

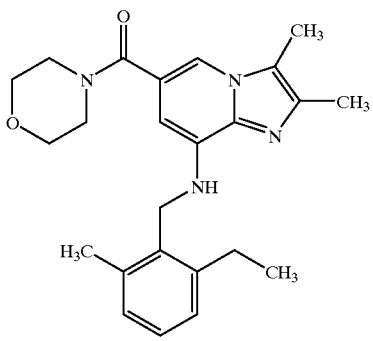

2,3-Dimethyl-8-(2-ethyl-6-methylbenzylamino)-imidazo[1,2-a]pyridine-6-carboxylic acid (0.15 g, 0.44 mmol) and o-Benzotriazol-1-yl-N,N,N',N'-Tetramethyluronium tetrafluoroborate (TBTU)(0.14 g, 0.44 mmol) were added to methylene chloride (10 ml). Morpholine (0.12 g, 1.4 mmol) was added and the reaction mixture was stirred at ambient temperature for 1.5 h. The reaction mixture was added to a column with silica gel and purification by chromatography using ethylacetate:methylene chloride (1:1) as eluent gave 0.12 g (66%) of the desired product.

$^1$H-NMR (300 MHz, CDCl$_3$): δ1.2 (t, 3H), 2.32 (s, 3H), 2.35 (s, 3H), 2.37 (s, 3H), 2.7 (q, 2H), 3.7 (s, 8H), 4.35 (d, 2H), 4.95 (bs, 1H), 6.15 (s, 1H), 7.0–7.2 (m, 3H), 7.4 (s, 1H)

Example 1.2

Synthesis of N-(4-ethoxyphenyl)-8-(2-ethyl-6-methylbenzylamino)-2,3-dimethylimidazo[1,2-a]pyridine-6-carboxamide

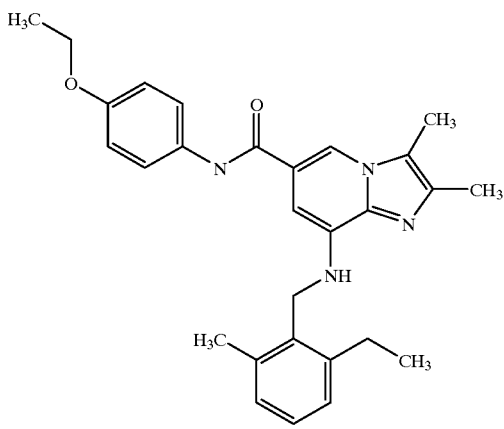

2,3-Dimethyl-8-(2-ethyl-6-methylbenzylamino)-imidazo[1,2-a]pyridine-6-carboxylic acid (0.15 g, 0.44 mmol) and o-Benzotriazol-1-yl-N,N,N',N'-Tetramethyluronium tetrafluoroborate (TBTU)(0.14 g, 0.44 mmol) were added to methylene chloride (10 ml). 4-ethoxyanilin(0.19 g, 1.4 mmol) was added and the reaction mixture was stirred at ambient temperature for 72 h. The solvent was evaporated under reduced pressure and the residue was added to a column with silica gel and was purified by chromatography using methylene chloride:methanol (95:5) as eluent. The residue was treated with a hot mixture of hexane:ethyl acetate (2:1) and the product was filtered off and dried to obtain 0.14 g (74%) of the desired compound as white crystals.

$^1$H-NMR (300 MHz, CDCl$_3$): δ1.2 (t, 3H), 1.4 (t,3H), 2.35 (s, 9H), 2.65 (q, 2H), 4.0 (q, 2H), 4.35 (d, 2H), 4.9 (t, 1H), 6.55 (s, 1H), 6.85 (d, 2H), 7.0–7.2 (m, 3H), 7.5 (d, 2H), 7.9 (s, 1H), 8.15 (s, 1H)

Example 1.3

Synthesis of N-[2-(dimethylamine)-2-oxoethyl]-8-(2-ethyl-6-methylbenzylamino)-N,2,3-trimethylimidazo[1,2-a]pyridine-6-carboxamide

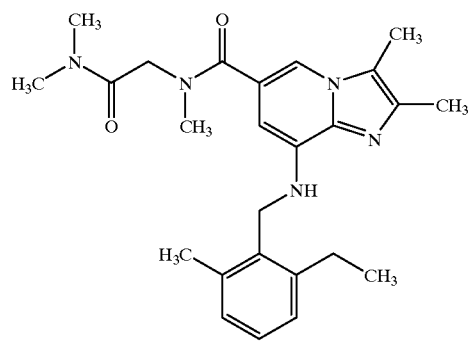

2,3-Dimethyl-8-(2-ethyl-6-methylbenzylamino)-imidazo[1,2-a]pyridine-6-carboxylic acid (0.13 g, 0.38 mmol) and o-Benzotriazol-1-yl-N,N,N',N'-Tetramethyluronium tetrafluoroborate (TBTU) (0.12 g, 0.38 mmol) were added to methylene chloride (10 ml). N,N.Dimethyl-2-methylaminoacetamide (0.088 g, 0.38 mmol) was added and the reaction mixture was stirred at ambient temperature for 1 h. The solvent was evaporated under reduced pressure and the residue was purified by column chromatography using methylene chloride:methanol as eluent (95:5) which gave 80 mg (48%) of the title product.

$^1$H-NMR (500 MHz, CDCl$_3$): δ1.2 (t, 3H), 2.3 (s, 6H), 2.35 (s, 3H), 2.65 (q, 2H), 2.75 (s, 6H), 2.95 (s, 3H), 3.15 (s, 2H), 4.35 (bs, 2H), 4.85 (bs, 1H), 6.25 (s, 1H), 7.0–7.2 (m, 3H), 7.45 (s, 1H).

Example 1.4

Synthesis of (8-(2-ethyl-6-methylbenzylamino)-2,3-dimethylimidazo[1,2-a]pyridin-yl)(4-methylpiperazino)methanone

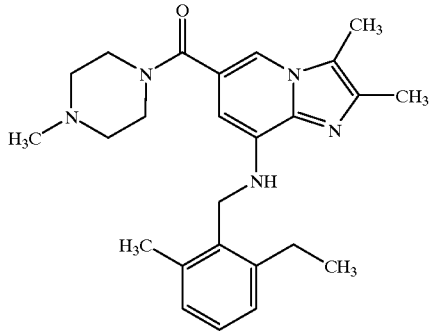

2,3-dimethyl-8-(2-ethyl-6-methylbenzylamino)-imidazo[1,2-a]pyridine-6-carboxylic acid (0.5 g, 1.48 mmol) and o-Benzotriazol-1-yl-N,N,N',N'-Tetramethyluronium tetrafluoroborate (TBTU)(0.48 g, 0.1.5 mmol) were added to methylene chloride (20 ml) and the mixture was stirred for 5 min. N-methylpiperazine (0.16 g, 1.6 mmol) was added and the reaction mixture was stirred at ambient temperature overnight. The solvent was evaporated under reduced pressure and purification of the residue by column chromatography on silica gel using methylene chloride:methanol (9:1) as eluent gave 0.46 g (74%) of the title compound.

$^1$H-NMR (500 MHz,CDCl$_3$): δ1.22 (t, 3H), 2.34 (s, 3H), 2.36 (s, 3H), 2.38 (s, 3H), 2.47 (bs, 4H), 2.71 (q, 2H), 2.80 (s, 3H), 3.65 (bs, 4H), 4.36 (d, 2H), 4.94 (t, 1H), 6.19 (s, 1H), 7.04–7.18 (m, 3H), 7.42 (s, 1H)

Example 1.5

Synthesis of 1-((8-(2-ethyl-6-methylbenzylamino)-2,3-dimethylimidazo[1,2-a]pyridin-6-yl)carbonyl)-2-(s)-pyrrolidinecarboxamide

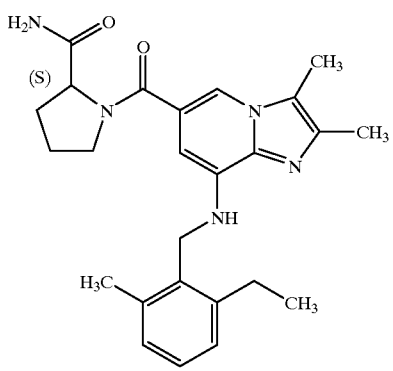

2,3-dimethyl-8-(2-ethyl-6-methylbenzylamino)-imidazo[1,2-a]pyridine-6-carboxylic acid (0.15 g, 0.44 mmol), o-Benzotriazol-1-yl-N,N,N',N'-Tetramethyluronium tetrafluoroborate (TBTU)(0.14 g, 0.45 mmol) and triethylamine (0.05 g, 0.5 mmol) were added to methylene chloride (10 ml) and the mixture was stirred for 10 min. (S)-prolinamide (0.016 g, 0.45 mmol) was added and the reaction mixture was stirred at ambient temperature for 1 h. The solvent was evaporated under reduced pressure and purification of the residue by column chromatography on silica gel using methylene chloride:methanol (9:1) as eluent and crystallization from diethyl ether gave 0.07 g (36%) of the title compound.

$^1$H-NMR (500 MHz,CDCl$_3$): δ1.21 (t, 3H), 2.1–2.2 (m, 4H), 2.33 (s, 3H), 2.35 (s, 3H), 2.37 (s, 3H), 2.70 (q, 2H), 3.65–3.75 (m, 2H), 4.36 (d, 2H), 4.80 (bs, 1H), 4.94 (bs, (1H), 5.88 (s, 1H), 6.33 (s, 1H), 6.98 (s, 1H), 7.04–7.19 (m,3H), 7.54 (s, 1H)

Example 1.6

Synthesis of 8-(2-ethyl-6-methylbenzylamino)-N-hydroxy-2,3-dimethylimidazo[1,2-a]pyridine-6-carboxamide

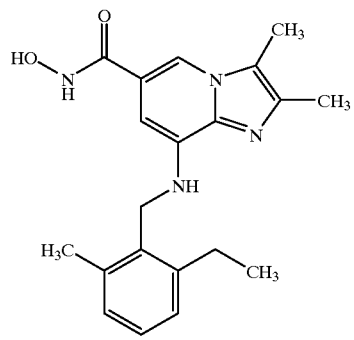

2,3-dimethyl-8-(2-ethyl-6-methylbenzylamino)-imidazo[1,2-a]pyridine-6-carboxylic acid (0.15 g, 0.45 mmol), o-Benzotriazol-1-yl-N,N,N',N'-Tetramethyluronium tetrafluoroborate (TBTU)(0.14 g, 0.45 mmol), triethylamine (0.1 g, 0.99 mmol) and hydroxylamine hydrochloride (0.031 g, 0.46 mmol) in dimethylformamide (5 ml).

The title compound were prepared according to Example 1.5 (Yield: 0.016 g, 10%)

$^1$H-NMR (500 MHz,CDCl$_3$): δ1.15 (bs, 3H), 2,25 (bs, 9H), 2.6 (bs, 2H), 4.25 (bs, 2H), 4.95 (bs, 1H), 6.45 (bs, 1H), 6.9–7.1 (m, 3H), 7.75 (bs, 1H)

Example 1.7

Synthesis of (2-ethyl-6 methylbenzylamino)-N-(2-(2-hydroxyethoxy)ethyl)-2,3-dimethylimidazo[1,2-a]pyridine-6-carboxamide

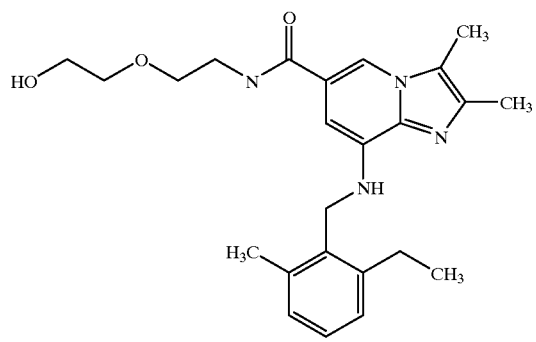

2,3-dimethyl-8-(2-ethyl-6-methylbenzylamino)-imidazo[1,2-a]pyridine-6-carboxylic acid (0.3 g, 0.88 mmol), o-Benzotriazol-1-yl-N,N,N',N'-Tetramethyluronium tetrafluoroborate (TBTU)(0.29 g, 0.90 mmol) and 2-(2-aminoethoxy)ethanol (0.2 g, 1.9 mmol) in methylene chloride (10 ml).

The title compound were prepared according to Example 1.5 (Yield: 0.24 g, 80%)

¹H-NMR (500 MHz,CDCl₃): δ1.25 (t, 3H), 2.25 (s, 3H), 2.3 (s, 3H), 2.35 (s, 3H), 2.75 (q, 2H), 3.4–3.45 (m, 2H), 3.55–3.7 (m, 6H), 4.35 (d, 2H), 5.05 (t, 1H), 6.45 (s,1H), 7.0–7.2 (m, 4H), 7.5 (s, 1H)

Example 1.8

Synthesis of (8-(2-ethyl-6-methylbenzylamino)-2,3-dimethylimidazo[1,2-a]pyridin-6-yl)(3-hydroxy-1-pyrrolidinyl)methanone

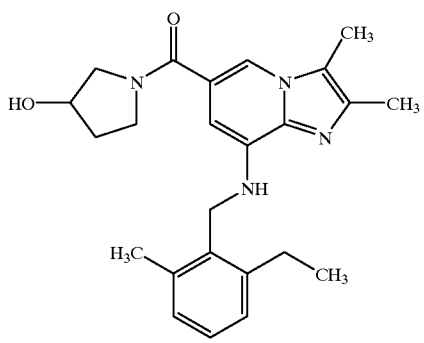

2,3-dimethyl-8-(2-ethyl-6-methylbenzylamino)-imidazo[1,2-a]pyridine-6-carboxylic acid (0.15 g, 0.44 mmol), o-Benzotriazol-1-yl-N,N,N',N'-Tetramethyluronium tetrafluoroborate (TBTU)(0.14 g, 0.44 mmol) and 3-pyrrolidinol (0.12 g, 1.4 mmol) in methylene chloride (10 ml).

The title compound were prepared according to Example 1.4. Crystallization from ethylacetate:hexane (2:1) (Yield: 0.24 g,80%)

¹H-NMR (300 MHz,CDCl₃): δ1.23 (t, 3H), 1.93 (bs, 2H), 2.33 (s, 3H), 2.34 (s,3H), 2.41 (s, 3H), 2.70 (q, 2H), 3.51–3.89 (m, 4H), 4.35 (d, 2H), 4.38–4.55 (m, 1H), 5.04 (bs, 1H), 6.35 (s, 1H), 7.01–7.16 (m, 3H), 7.51 (s, 1H)

Example 1.9

Synthesis of N-(3,4-dihydroxyphemethyl)-8-(2-ethyl-6-methylbenzylamino)-2,3-dimethylimidazo[1,2-a]pyridine-6-carboxamide

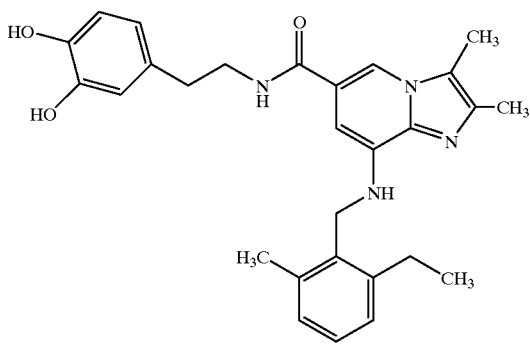

2,3-dimethyl-8-(2-ethyl-6-methylbenzylamino)-imidazo[1,2-a]pyridine-6-carboxylic acid (0.15 g, 0.44 mmol) and o-Benzotriazol-1-yl-N,N,N',N'-Tetramethyluronium tetrafluoroborate (TBTU)(0.14 g, 0.45 mmol) were added to dimethylformamide(10 ml) and the mixture was stirred for 5 min. 3,4-dihydroxyphenetylamin (0.27 g 1.4 mmol) and triethylamine (0.28 g, 1.4 mmol) were added was added and the reaction mixture was stirred at ambient temperature for 72 h. The solvent was evaporated under reduced pressure and purification of the residue by column chromatography on silica gel using methylene chloride:methanol (9:1) as eluent and crystallization from acetonitrile gave 0.059 g (28%) of the title compound.

¹H-NMR (400 MHz,DMSO-d₆): δ1.15 (t, 1H), 2.22 (s, 3H), 2.33 (s, 3H), 2.37 (s, 3H), 2.65–2.74 (m, 4H), 3.41 (q, 2H), 4.37 (d, 2H), 4.85 (t, 1H), 6.48 (dd, 1H), 6.63–6.66 (m, 2H), 6.70 (d, 1H), 7.07–7.21 (m, 3H), 8.04 (d, 1H), 8.49 (t, 1H), 8.63 (s, 1H), 8.75 (s, 1H)

Example 1.10

Synthesis of 8-(2-ethyl-6-methylbenzylamino-3-(hydroxymethyl)-2-methyl-6-(morpholinocarbonyl)-imidazo[1,2-a]pyridine

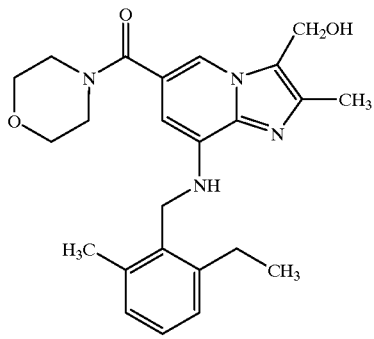

8-(2-ethyl-6-methylbenzylamino)-3-hydroxymethyl-2-methylimldazo[1,2-a]pyridine-6-carboxylic acid (0.012 g, 0.034 mmol), o-Benzotriazol-1-yl-N,N,N',N'-Tetramethyluronium tetrafluoroborate (TBTU)(0.011 g, 0.034 mmol) and morpholine (0.009 g, 0.1 mmol) in methylene chloride (1 ml)

The title compound were prepared according to Example 1.1. (Yield: 0.008 g, 56%)

¹H-NMR (300 MHz,DMSO-d₆): δ1.23 (t, 3H), 2.33 (s, 3H), 2.39 (s, 3H), 2.72 (q, 2H), 3.74 (bs, 8H), 4.37 (d, 2H), 4.85 (s, 2H), 5.02 (t, 1H), 6.27 (d, 1H), 7.06–7.22 (m,3H), 7.75 (d, 1H)

Example 1.86

Synthesis of N-((8-(2-ethyl-6-methylbenzyl)amino)-2,3-dimethylimidazo[1,2-a]pyridin-6-yl)carbonyl) guanidine

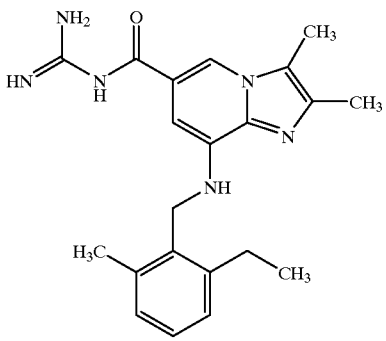

2,3-dimethyl-8-(2-ethyl-6-methylbenzylamino)-imidazo[1,2-a]pyridine-6-carboxylic acid (0.5 g, 1.5 mmol), diisopropyethylamin (0.57 g, 1.5 mmol) and guanidine carbonate (0.53 g, 2.9 mmol) were added to dimethylformamide (10 ml). o-Benzotriazol-1-yl-N,N,N',N'-Tetramethyluronium tetrafluoroborate (TBTU)(0.48 g, 1.5 mmol) was added and the reaction mixture was stirred at 50° C. for 3 h. The solvent was evaporated under reduced pressure and purification of the residue by column chromatography on silica gel using methylene chloride:methanol (100:15) as eluent and crystallization from diethyl ether gave 0.12 g (21%) of the title compound.

$^1$H-NMR (500 MHz,CDCl$_3$): δ1.1 (t, 3H), 2.25 (s, 3H), 2.3 (s, 3H), 2.35 (s, 3H), 2.7 (q, 2H), 4.35 (d, 2H), 4.8 (bs, 1H), 6.9 (s, 1H), 7.05–7.2 (m, 3H), 8.25 (s, 1H)

Example 1.87

Synthesis of 4-(2-(((8-(2-ethyl-6-methylbenzylamino)-2,3-dimethylimidazo[1,2-a]pyridin-6-yl)carbonyl)amino)ethoxy)-4-oxobutanoic acid

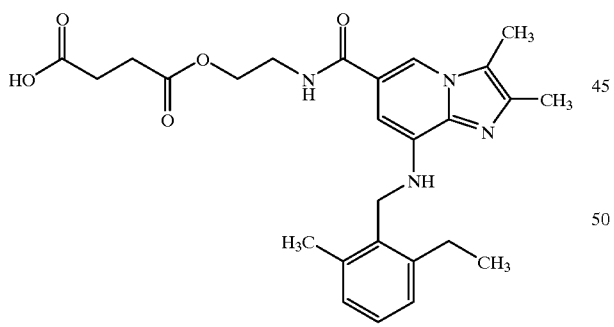

2,3 dimethyl-8-(2-ethyl-6-methylbenzylamino)-N-hydroxyethyl-imidazo[1,2-a]pyridine-6-carboxamide (250 mg, 0.263 mmol) and succinic anhydride (100 mg, 1.00 mmol) were added to 7 ml of acetone. The mixture was refluxed for 48 h. The presiptated product was filtered off and washed with acetone and ether to give 288 mg (91%) of the title compound.

$^1$H-NMR (500 MHz, DMSO): δ1.16 (t, 3H), 2.24 (s, 3H), 2.35 (s, 3H), 2.39 (s, 3H), 2.48–2.58 (m, 4H), 2.70 (q, 2H), 3.54 (q, 2H), 4.19 (t, 2H), 4.39 (d, 2H), 4.90 (t, 1H), 6.72 (s, 1H), 7.09–7.22 (m, 3H), 8.08 (s, 1H), 8.59 (t, 1H), 12.25 (s, 1H).

Example 11–85 was prepared by parallell-synthesis using the following method:

SCHEME 1

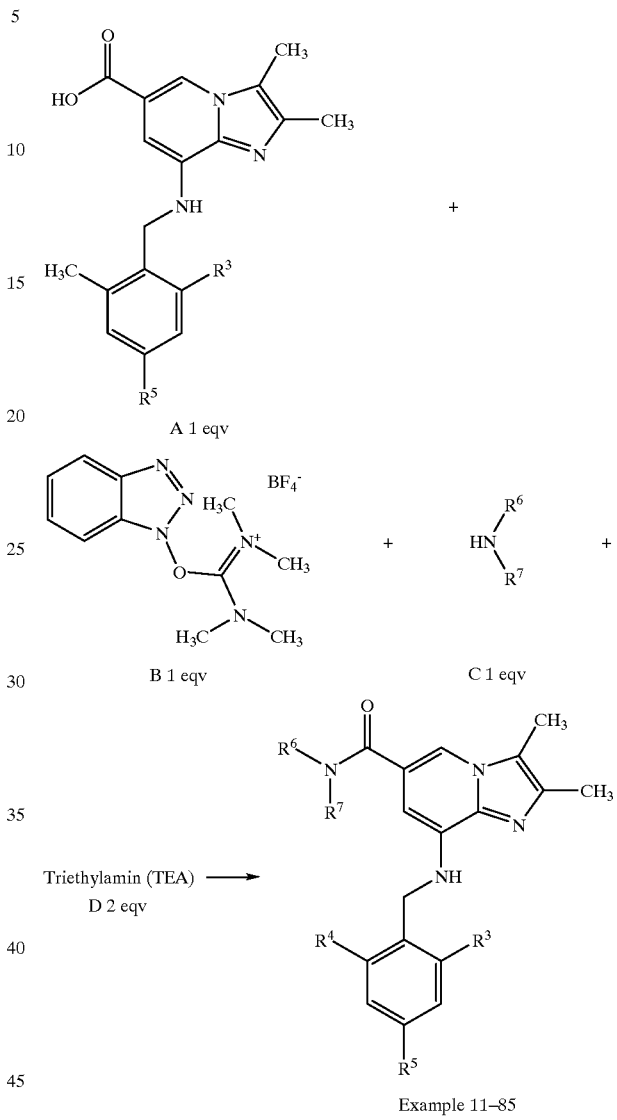

Example 11–85

Solution A: 0.149 mmol in 1 ml dimethylformamide

Solution B (TBTU): 0.297 mmol in 1 ml dimethylformamide

Solution C+D: Amin (C) (0.297 mmol in 1 ml dimethylformamide)+TEA (D) (0.594 mmol in 1 ml dimethylamin)

To a solution A (300 µl) were added solution B (150 µl) and solution C+D (150 µl). The reaction was stirred by shaking at room temperature overnight. The solvent was evaporated under reduced pressure. The residue was solved in dichloromethane/methanol (9/1)(600 µl) and was filtered through a plug of silca gel (100 mg) and the gel was washed with dichloromethane/methanol (9/1) (0.5–1.0 ml). The filtrate was evaporated under reduced pressure to give the desired compounds. (If needed the compounds were purified by preparative HPLC.)

The analyses of the examples was made by HPLC and the compounds were identified by LC-mass spectroscopy. All compounds prepared in Example 11–85 showed a mass spectrum that confirmed the proposed structure.

As the starting compound A in the reactions the following compounds were used.
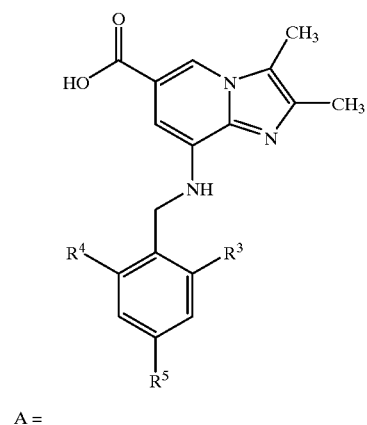
A =
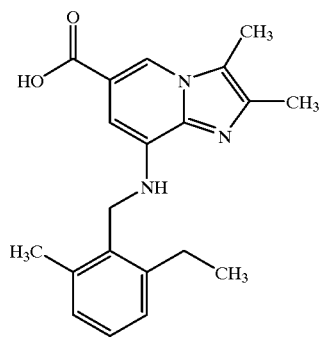
A1
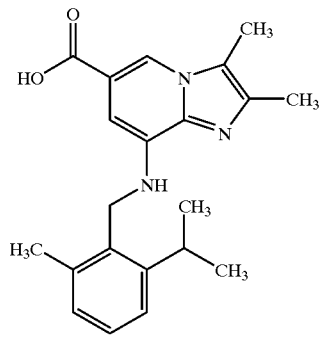
A2
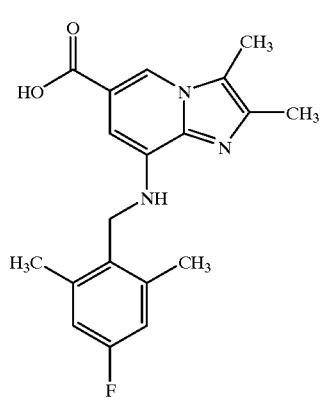
A3
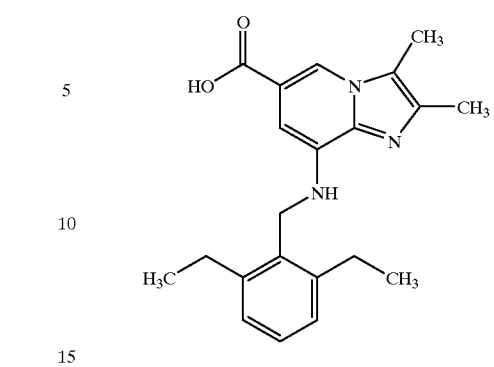
A4
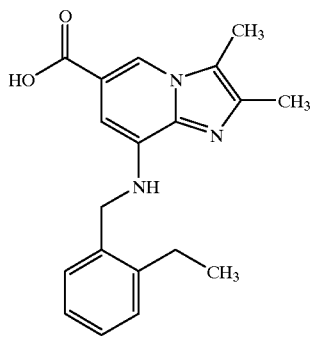
A5
As the starting compound C in the reaction the following amines were used.
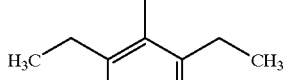
C =
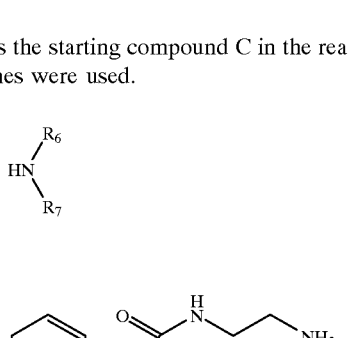
C1
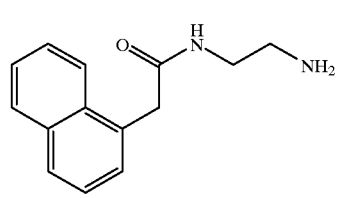
C2
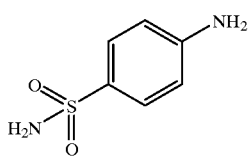
C3
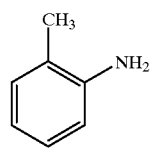
C4

-continued
C5 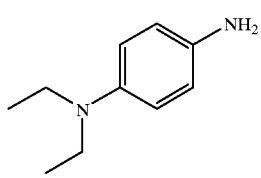
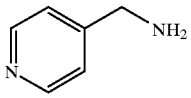 C5
C6 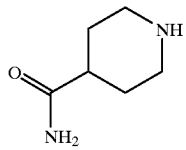
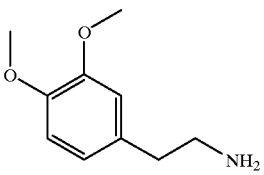 C16
C7 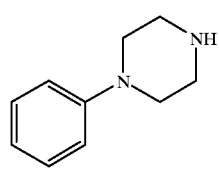
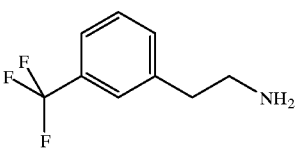 C17
C8 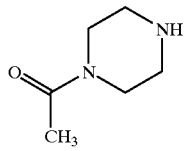
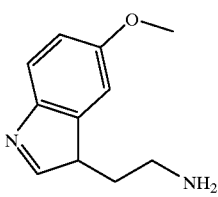 C18
C9 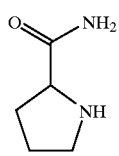
The Examples 11–85 were prepared according to scheme 1.
The primary or the secondary amino nitrogen is the nitrogen involved in the reaction.
e.g. A1+C5→Example 27
C10 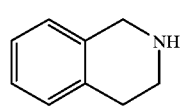
C11 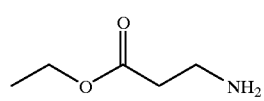
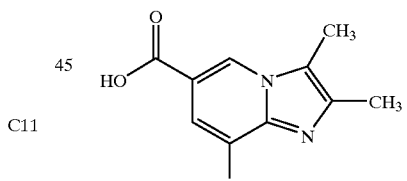
+
C12 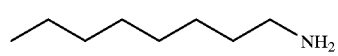
A1
C13 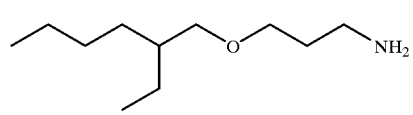
C14 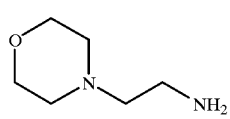
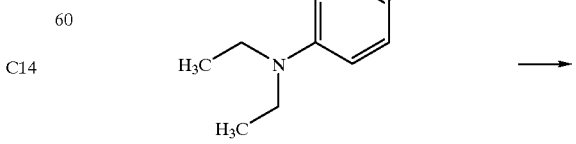
C5

-continued

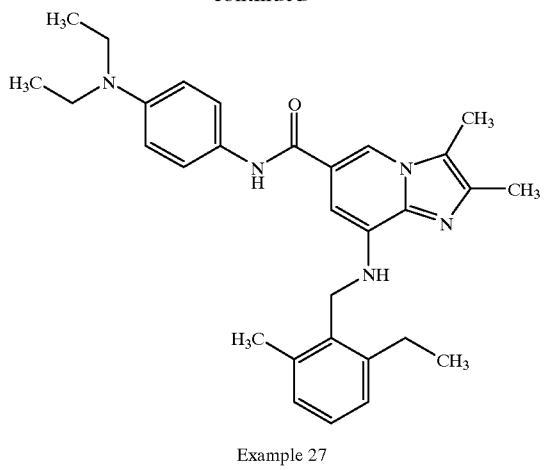

Example 27

An+C$_n$→Example 11–85

| | A1 | A2 | A3 | A4 | A5 |
|---|---|---|---|---|---|
| C1 | Example 11 | Example 12 | Example 13 | Example 14 | Example 15 |
| C2 | Example 16 | Example 17 | Example 18 | Example 19 | Example 20 |
| C3 | — | — | — | — | Example 21 |
| C4 | Example 22 | Example 23 | Example 24 | Example 25 | Example 26 |
| C5 | Example 27 | Example 28 | Example 29 | Example 30 | Example 31 |
| C6 | Example 32 | Example 33 | Example 34 | Example 35 | Example 36 |
| C8 | Example 37 | Example 38 | Example 39 | Example 40 | Example 41 |
| C9 | Example 42 | Example 43 | Example 44 | Example 45 | Example 46 |
| C10 | Example 47 | Example 48 | Example 49 | Example 50 | Example 51 |
| C11 | — | Example 52 | Example 53 | Example 54 | Example 55 |
| C12 | — | Example 56 | Example 57 | Example 58 | Example 59 |
| C13 | — | Example 60 | Example 61 | Example 62 | Example 63 |
| C14 | — | — | Example 64 | Example 65 | Example 66 |
| C15 | Example 67 | Example 68 | Example 69 | Example 70 | Example 71 |
| C16 | — | Example 72 | Example 73 | Example 74 | Example 75 |
| C17 | Example 76 | Example 77 | Example 78 | Example 79 | Example 80 |
| C18 | Example 81 | Example 82 | Example 83 | Example 84 | Example 85 |

2. Preparation of Intermediates

Example 2.1

Synthesis of 8-(2-ethylbenzylamino)-2,3-dimethylimidazo[1,2-a]pyridine-6-carboxylic acid 8-(2-ethylbenzylamino)-2,3-dimethylimidazo[1,2-a] pyridine-6-carboxamide (1.0 g, 0.0031 mol) and sodium hydroxide (1.2 g, 0.031 mol) were solved in ethanol (95%) (30 ml) and was refluxed overnight. The solvent was evaporated under reduced pressure and to the residue was added water. The pH was adjusted to 7 by addition of conc HCl (2.6 ml) and the solid that precipitated was isolated by filtration, washed with water and dried to give 1.0 g (99%) of the title compound.

$^1$H-NMR (300 MHz,DMSO-d$_6$): δ1.2 (t, 3H), 2.25 (s, 3H), 2.35 (s, 3H), 2.7 (q, 2H), 4.45 (d, 2H), 6.3 (s, 1H), 6.45 (t, 1H), 7.05–7.25 (m, 4H), 7.95 (s, 1H)

Example 2.2

Synthesis of 8-(2,6-diethylbenzylamino)-2,3-dimethylimidazo[1,2-a]pyridine-6-carboxylic acid 8-(2,6-diethylbenzylamino)-2,3-dimethylimidazo[1,2-a] pyridine-6-carboxamide (1.5 g, 0.0043 mol) and sodium hydroxide (1.7 g, 0.043 mol) were solved in ethanol (95%) (30 ml).

The title compound were prepared according to Example 1.4. (Yield: 1.5 g, 99%)

$^1$H-NMR (400 MHz,DMSO-d$_6$): δ1.14 (t, 6H), 2.22 (s, 3H), 2.37 (s, 3H), 2.67 (q, 4H), 4.37 (d, 2H), 4.89 (t, 1H), 6.68 (s, 1H), 7.11 (d, 2H), 7.23 (t, 1H), 8.09 (s, 1H)

Example 2.3

Synthesis of 8-(2,6-dimethyl-4-fluorobenzylamino)-2,3-dimethylimidazo[1,2-a]pyridine-6-carboxylic acid 8-(2,6-dimethyl-4-fluorobenzylamino)-2,3-dimethylimidazo[1,2-a]pyridine-6-carboxamide mesylate (1.47 g, 0.0034 mol) and sodium hydroxide (1.7 g, 0.034 mol) were solved in ethanol (95%) (30 ml).

The title compound were prepared according to Example 2.1. (Yield: 1.1 g, 95%).

$^1$H-NMR (400 MHz,DMSO-d$_6$): δ2.23 (s, 3H), 2.34 (s, 6H), 2.36 (s, 3H), 4.31 (d, 2H), 5.04 (bs, 1H), 6.70 (s, 1H), 6.90 (d, 2H), 8.02 (s, 1H)

Example 2.4

Synthesis of 8-(2-isopropyl-6-methylbenzylamino)-2,3-dimethylimidazo[1,2-a]pyridine-6-carboxylic acid 8-(2-isopropyl-6-methylbenzylamino)-2,3-dimethylimidazo[1,2-a]pyridine-6-carboxamide mesylate (1.2 g, 0.0027 mol) and sodium hydroxide (1.1 g, 0.027 mol) were solved in ethanol(95%) (25 ml).

The title compound were prepared according to Example 2.1. (Yield: 1.1 g, 95%)

$^1$H-NMR (300 MHz,DMSO-d$_6$): δ1.69 (d, 6H), 2.74 (s, 3H), 2.85 (s, 3H), 2.89 (s, 3H), 3.73 (m, 1H), 4.90 (d, 2H), 5.48 (t, 1H), 7.19 (s, 1H), 7.55–7.61 (m, 1H), 7.70–7.76 (m, 2H), 8.60 (s, 1H)

Example 2.5

Synthesis of 8-(2-ethyl-6-methylbenzylamino)-2,3-dimethylimidazo[1,2-a]pyridine-6-carboxylic acid 8-(2-ethyl-6-methylbenzylamino)-2,3-dimethylimidazo [1,2-a]pyridine-6-carboxamide mesylate (11.0 g, 0.025 mol) and sodium hydroxide (7.0 g, 0.17 mol) were solved in ethanol(95%) (120 ml) and was refluxed for 20 h. The solvent was evaporated under reduced pressure and to the residue was added water (150 ml). The pH was adjusted to 5 by addition of conc HCl and acetic acid and the solid that precipitated was isolated by filtration, washed with water and acetone, and dried to give 7.6 g (88%) of the title compound.

¹H-NMR (500 MHz,DMSO-d₆): δ1.15 (t, 3H), 2.26 (s, 3H), 2.34 (s, 3H), 2.39 (s, 3H), 2.69 (q, 2H), 4.38 (d, 2H), 5.2 (bs, 1H), 6.73 (s, 1H), 7.07–7.2 (m, 3H), 8.12 (s, 1H)

Example 2.6

Synthesis of 8-(2-ethyl-6-methylbenzylamino)-3-hydroxymethyl-2-methylimidazo[1,2-a]pyridine-6-carboxylic acid 8-(2-ethyl-6-methylbenzylamino)-3-hydroxymethyl-2-methylimidazo[1,2-a]pyridine-6-carboxamide (0.02 g, 0.057 m mol) and sodium hydroxide (0.02 g, 0.29 mmol) were solved in ethanol (95%) (1 ml) and was refluxed for 20 h. The solvent was evaporated under reduced pressure and to the residue was added water (1 ml). The pH was adjusted to 5 by addition of acetic acid and the solid that precipitated was isolated by filtration, washed with water and dried to give 0.012 g (60%) of the title compound.

¹H-NMR (300 MHz,DMSO-d₆): δ1.14 (t, 3H), 2.22 (s, 3H), 2.33 (s, 3H), 2.67 (q, 2H), 4.33 (d, 2H), 4.55 (bs, 1H), 4.67 (s, 2H), 6.83 (s, 1H), 7.06–7.24 (m, 3H), 8.15 (s, 1H)

Biological Tests

1. In vitro Experiments

Acid Secretion Inhibition in Isolated Rabbit Gastric Glands

Inhibiting effect on acid secretion in vitro in isolated rabbit gastric glands was measured as described by Berglindh et al. (1976) Acta Physiol. Scand. 97, 401–414.

Determination of H⁺,K⁺-ATPase Activity

Membrane vesicles (2.5 to 5 μg) were incubated for 15 min at +37° C. in 18 mM Pipes/Tris buffer pH 7.4 containing 2 mM MgCl₂, 10 mM KCl and 2 mM ATP. The ATPase activity was estimated as release of inorganic phosphate from ATP, as described by LeBel et al. (1978) Anal. Biochem. 85, 86–89.

2. In vivo Experiments

Inhibiting Effect on Acid Secretion in Female Rats

Female rats of the Sprague-Dawly strain are used. They are equipped with cannulated fistulae in the stomach (lumen) and the upper part of the duodenum, for collection of gastric secretions and administration of test substances, respectively. A recovery period of 14 days after surgery is allowed before testing commenced.

Before secretory tests, the animals are deprived of food but not water for 20 h. The stomach is repeatedly washed through the gastric cannula with tap water (+37° C.), and 6 ml Ringer-Glucose given subcutaneously. Acid secretion is stimulated with infusion during 2.5–4 h (1.2 ml/h, subcutaneously) of pentagastrin and carbachol (20 and 110 nmol/kg·h, respectively), during which time gastric secretions are collected in 30-min fractions. Test substances or vehicle are given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4–6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.

Bioavailability in Rat

Adult rats of the Sprague-Dawley strain are used. One to three days prior to the experiments all rats are prepared by cannulation of the left carotid artery under anaesthesia. The rats used for intravenous experiments are also cannulated in the jugular vein (Popovic (1960) J. Appl. Physiol. 15, 727–728). The cannulas are exteriorized at the nape of the neck.

Blood samples (0.1–0.4 g) are drawn repeatedly from the carotid artery at intervals up to 5.5 hours after given dose. The samples are frozen until analysis of the test compound.

Bioavailability is assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, is determined by the log/linear trapezoidal rule and extrapolated to infinity by dividing the last determined blood concentration by the elimination rate constant in the terminal phase. The systemic bioavailability (F %) following intraduodenal or oral administration is calculated as F(%)= (AUC (p.o. or i.d.)/AUC (i.v.) )×100.

Inhibition of Gastric Acid Secretion and Bioavailability in the Conscious Dog

Labrador retriever or Harrier dogs of either sex are used. They are equipped with a duodenal fistula for the administration of test compounds or vehicle and a cannulated gastric fistula or a Heidenhaim-pouch for the collection of gastric secretion.

Before secretory tests the animals are fasted for about 18 h but water is freely allowed. Gastric acid secretion is stimulated for up to 6.5 h infusion of histamine dihydrochloride (12 ml/h) at a dose producing about 80% of the individual maximal secretory response, and gastric juice collected in consecutive 30 min fractions. Test substance or vehicle is given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples are determined by titration to pH 7.0, and the acid output calculated. The acid output in the collection periods after administration of test substance or vehicle are expressed as fractional responses, setting the acid output in the fraction preceding administration to 1.0. Percentage inhibition is calculated from fractional responses elicited by test compound and vehicle.

Blood samples for the analysis of test compound concentration in plasma are taken at intervals up to 4 h after dosing. Plasma is separated and frozen within 30 min after collection and later analyzed. The systemic bioavailability (F %) after oral or i.d. administration is calculated as described above in the rat model.

What is claimed is:

1. A compound of the formula I

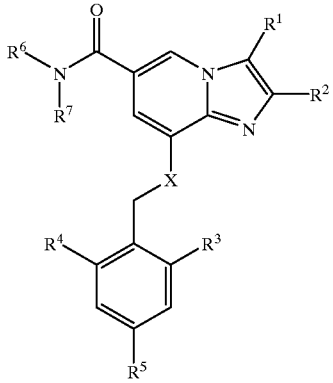

or a pharmaceutically acceptable salt thereof, wherein $R^1$ is
(a) H,
(b) $CH_3$, or
(c) $CH_2OH$;

$R^2$ is
(a) $CH_3$, or
(b) $CH_2CH_3$;

$R^3$ is
(a) H,
(b) $C_1$–$C_6$ alkyl,
(c) hydroxylated $C_1$–$C_6$ alkyl, or
(d) halogen;

$R^4$ is
(a) H,
(b) $C_1$–$C_6$ alkyl,
(c) hydroxylated $C_1$–$C_6$ alkyl, or
(d) halogen;

$R^5$ is
(a) H, or
(b) halogen;

$R^6$ and $R^7$ are independently selected substituents, comprising C, H, N, O, S, Se, P or Halogen atoms, which give compounds of Formula I a molecular weight $\leq 600$, provided that at least one of $R^6$ and $R^7$ can not be H, $C_1$–$C_6$ alkyl, hydroxylated $C_1$–$C_6$ alkyl, or $C_1$–$C_6$ alkoxy-substituted $C_1$–$C_6$ alkyl; and X is
(a) NH, or
(b) O.

2. A compound according to Formula I

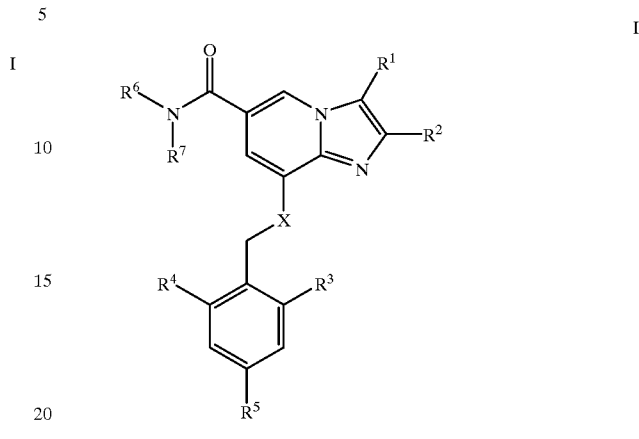

or a pharmaceutically acceptable salt thereof wherein $R^1$ is $CH_3$ or $CH_2OH$; $R^2$ is $CH_3$ or $CH_2CH_3$; $R^3$ is $CH_3$ or $CH_2CH_3$; $R^4$ is $CH_3$ or $CH_2CH_3$; $R^5$ is H, Br, Cl, or F; and $R^6$ and $R^7$ are independently (provided that at least one of $R^6$ and $R^7$ can not be H, $C_1$–$C_6$ alkyl, hydroxylated $C_1$–$C_6$ alkyl or $C_1$–$C_6$ alkoxy-substituted $C_1$–$C_6$ alkyl)

(a) H,
(b) $C_1$–$C_6$ alkyl,
(c) hydroxylated $C_1$–$C_6$ alkyl,
(d) $C_1$–$C_6$ alkoxy-substituted $C_1$–$C_6$ alkyl,
(e) $C_2$–$C_6$ alkenyl,
(f) $C_2$–$C_6$ alkynyl,
(g) halogenated $C_1$–$C_6$ alkyl,
(h) $C_3$–$C_8$ cycloalkyl,
(i) cycloalkyl-substituted $C_1$–$C_6$ alkyl,
(j) aryl, in which aryl represents phenyl, pyridyl, thienyl, imidazolyl, indolyl, naphthyl or furanyl, optionally substituted by one or more substituents selected from halogen, $C_1$–$C_6$ alkyl, $C_1$–$C_6$ alkoxy, $CF_3$, OH, nitro, amino, $C_1$–$C_6$ alkyl-NH—, ($C_1$–$C_6$ alkyl)$_2$—N—, CN or $NH_2SO_2$,
(k) aryl substituted $C_1$–$C_6$ alkyl, in which aryl represents phenyl, pyridyl, thienyl, imidazolyl, indolyl, naphthyl or furanyl, optionally substituted with one or more substituents selected from halogen, $C_1$–$C_6$ alkyl, $C_1$–$C_6$ alkoxy, $CF_3$, OH, nitro, amino, $C_1$–$C_6$ alkyl-NH—, ($C_1$–$C_6$ alkyl)$_2$—N—, CN or $NH_2SO_2$,
(l) $R^8$—($C_1$–$C_6$) alkyl-, wherein $R^8$ is $NH_2C$=O—, $C_1$–$C_6$ alkyl-NHC=O—, ($C_1$–$C_6$ alkyl)$_2$NC=O—, $C_1$–$C_6$ alkyl-OOC—, $NH_2SO_2$—, $C_1$–$C_6$ alkyl-$SO_2NH$—, $ArSO_2NH$—, cyano, $C_1$–$C_6$ alkyl-CO—NH—, $C_1$–$C_6$ alkyl-OOCNH—, $C_1$–$C_6$ alkyl-O—, $C_7$–$C_{12}$ alkyl-O—, $C_1$–$C_6$ alkyl-SO—, $C_1$–$C_6$ alkyl-S—, $C_1$–$C_6$ alkyl-$SO_2$—, $C_1$–$C_6$ alkyl-C=O—, $NH_2$—, $C_1$–$C_6$ alkyl-NH—, ($C_1$–$C_6$ alkyl)$_2$N—, ArCONH—, Ar($C_1$–$C_6$ alkyl)CONH, ArNHSO$_2$—, (Ar)$_2$—N—SO$_2$—, $C_1$–$C_6$ alkyl-NHSO$_2$—, ArS—, ArSO—, ArSO$_2$—, ArC=O—, $NH_2CONH$—, $C_1$–$C_6$ alkyl-NHCONH—, ($C_1$–$C_6$ alkyl)$_2$—NCONH—, ArNHCONH—, ($C_1$–$C_6$ alkyl)$_2$—N—SO$_2$—, Ar—O—, Ar—NH—, Ar($C_1$–$C_6$ alkyl)N—, hydroxylated $C_1$–$C_6$ alkyl-O— or morpholinyl; wherein Ar represents phenyl, pyridyl, thienyl, imidazolyl, indolyl, naphthyl or furanyl, optionally substituted with one or more substituents selected from halogen, $C_1$–$C_6$ alkyl, $C_1$–$C_6$ alkoxy, $CF_3$, OH, CN, nitro, amino, $C_1$–$C_6$ alkyl-NH—, or ($C_1$–$C_6$ alkyl)$_2$N—, (m) $C_7$–$C_{12}$ alkyl, (n) OH, O—$C_1$–$C_6$ alkyl, or O-hydroxylated $C_1$–$C_6$ alkyl, (o)

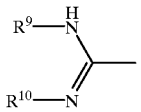

wherein $R^9$ and $R^{10}$ are independently H or $C_1$–$C_6$ alkyl, (p) $R^{11}$—($C_1$–$C_6$) alkyl-COO—($C_1$–$C_6$) alkyl- wherein $R^{11}$ is HOOC—, $C_1$–$C_6$ alkyl-OOC— or an amino carbonyl group with the formula

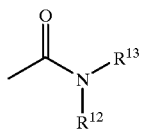

wherein $R^{12}$ and $R^{13}$ are the same or different and selected from H, or $C_1$–$C_6$ alkyl, or (q) $R^6$ and $R^7$, together with the nitrogen atom to which they are attached, form a saturated or unsaturated ring optionally containing one or more further heteroatoms, optionally substituted with one or more substituents selected from halogen, $C_1$–$C_6$ alkyl, $C_1$–$C_6$ alkoxy, $CF_3$, OH, nitro, amino, $C_1$–$C_6$ alkyl-NH—, ($C_1$–$C_6$ alkyl)$_2$—N—, CN, $NH_2SO_2$, phenyl, $NH_2CO$— and $C_1$–$C_6$ alkyl-CO—, which saturated or unsaturated ring can be fused with an aromatic ring.

3. A compound or salt thereof according to claim 2 wherein $R^1$ is $CH_3$ or $CH_2OH$; $R^2$ is $CH_3$; $R^3$ is $CH_3$ or $CH_2CH_3$; $R^4$ is $CH_3$ or $CH_2CH_3$; $R^5$ is H, Br, Cl, or F; and $R^6$ and $R^7$ are independently (provided that at least one of $R^6$ and $R^7$ can not be H, $C_1$–$C_6$ alkyl, hydroxylated $C_1$–$C_6$ alkyl or $C_1$–$C_6$ alkoxy-substituted $C_1$–$C_6$ alkyl)

(a) H, (b) $C_1$–$C_6$ alkyl, (c) hydroxylated $C_1$–$C_6$ alkyl, (d) $C_1$–$C_6$ alkoxy-substituted $C_1$–$C_6$ alkyl, (e) halogenated $C_1$–$C_6$ alkyl, (f) aryl, in which aryl represents phenyl, pyridyl, imidazolyl, indolyl, or naphthyl, optionally substituted by one or more substituents selected from halogen, $C_1$–$C_6$ alkyl, $C_1$–$C_6$ alkoxy, $CF_3$, OH, $C_1$–$C_6$ alkyl-NH—, ($C_1$–$C_6$ alkyl)$_2$—N—, or CN—, (g) aryl substituted $C_1$–$C_6$ alkyl, in which aryl represents phenyl, pyridyl, imidazolyl, indolyl, or naphthyl, optionally substituted with one or more substituents selected from halogen, $C_1$–$C_6$ alkyl, $C_1$–$C_6$ alkoxy, $CF_3$, or OH, (h) $R^8$—($C_1$–$C_6$ alkyl)-, wherein $R^8$ is $NH_2C=O$—, $C_1$–$C_6$ alkyl-NHC=O—, ($C_1$–$C_6$ alkyl)$_2$NC=O—, $C_1$–$C_6$ alkyl-OOC—, cyano, $C_1$–$C_6$ alkyl-CO—NH—, $C_1$–$C_6$ alkyl-OOCNH—, $C_1$–$C_6$ alkyl-O—, $C_7$–$C_{12}$ alkyl-O—, $C_1$–$C_6$ alkyl-SO—, $C_1$–$C_6$ alkyl-S—, $C_1$–$C_6$ alkyl-C=O—, —ArCONH—, Ar($C_1$–$C_6$ alkyl)CONH, ArC=O—, $NH_2CONH$—, $C_1$–$C_6$ alkyl-NHCONH—, ($C_1$–$C_6$ alkyl)$_2$—NCONH—, ArNHCONH—, hydroxylated $C_1$–$C_6$ alkyl-O— or morpholinyl; wherein Ar represents phenyl, pyridyl, imidazolyl, indolyl, or naphthyl optionally substituted with one or more substituents selected from halogen, $C_1$–$C_6$ alkyl, $C_1$–$C_6$ alkoxy, $CF_3$, OH and CN, (i) $C_7$–$C_{12}$ alkyl, (j) OH, (k) $R^{11}$—($C_1$–$C_6$) alkyl-COO—($C_1$–$C_6$) alkyl- wherein $R^{11}$ is HOOC—, or $C_1$–$C_6$ alkyl-OOC, or (l) $R^6$ and $R^7$, together with the nitrogen atom to which they are attached, form a saturated or unsaturated ring optionally containing one or more further heteroatoms, optionally substituted with one or more substituents selected from halogen, $C_1$–$C_6$ alkyl, $C_1$–$C_6$ alkoxy, $CF_3$, OH, nitro, amino, CN, $NH_2SO_2$, phenyl, $NH_2CO$— and $C_1$–$C_6$ alkyl-CO—, which saturated or unsaturated ring can be fused with an aromatic ring.

4. The compound according to claim 1 or 2 which is
2,3-dimethyl-8-(2-ethyl-6-methylbenzylamino)-6-(morpholinocarbonyl)-imidazo[1,2-a]pyridine,
N-(4-ethoxyphenyl)-8-(2-ethyl-6-methylbenzylamino)-2,3-dimethylimidazo[1,2-a]pyridine-6-carboxamide,
N-[2-(dimethylamino)-2-oxoethyl]-8-(2-ethyl-6-methylbenzylamino)-N,2,3-trimethylimidazo[1,2-a]pyridine-6-carboxamide,
(8-(2-ethyl-6-methylbenzylamino)-2,3-dimethylimidazo[1,2-a]pyridin-yl)(4-methylpiperazino)methanone,
1-((8-(2-ethyl-6-methylbenzylamino)-2,3-dimethylimidazo[1,2-a]pyridin-6-yl)carbonyl)-2-(s)-pyrrolidinecarboxamide,
8-(2-ethyl-6-methylbenzylamino)-N-hydroxy-2,3-dimethylimidazo[1,2-a]pyridine-6-carboxamide,
(2-ethyl-6-methylbenzylamino)-N-(2-(2-hydroxyethoxy)ethyl)-2,3-dimethylimidazo[1,2-a]pyridine-6-carboxamide,
(8-(2-ethyl-6-methylbenzylamino)-2,3-dimethylimidazo[1,2-a]pyridin-6-yl)(3-hydroxy-1-pyrrolidinyl)methanone,
N-(3,4-dihydroxyphenethyl)-8-(2-ethyl-6-methylbenzylamino)-2,3-dimethylimidazo[1,2-a]pyridine-6-carboxamide,
8-(2-ethyl-6-methylbenzylamino)-3-(hydroxymethyl)-2-methyl-6-(morpholinocarbonyl)-imidazo[1,2-a]pyridine,
N-((8-(2-ethyl-6-methylbenzylamino)-2,3-dimethylimidazo[1,2-a]pyridin-6-yl)carbonyl)guanidine,
4-(2-(((8-(2-ethyl-6-methylbenzylamino)-2,3-dimethylimidazo[1,2-a]pyridin-6-yl)carbonyl)amino)ethoxy)-4-oxobutanoic acid, or a pharmaceutically acceptable salt thereof.

5. A compound according to claim 1 or 2 as a hydrochloride or mesylate salt.

6. A product containing a compound or salt thereof according to any one of claims 1–3 and at least one antimicrobial agent as a combined preparation for simultaneous, separate or sequential use in the prevention or treatment of gastrointestinal inflammatory diseases.

7. A product containing a compound or salt thereof according to any one of claims 1–3 and at least one proton pump inhibitor as a combined preparation for simultaneous, separate or sequential use in the prevention or treatment of gastrointestinal inflammatory diseases.

8. A process for the preparation of a compound according to any one of claims 1 to 3, wherein X is NH and $R^1$ is H or $CH_3$, comprising (a) reacting a compound of the Formula V

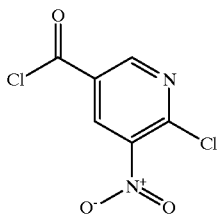

V with an alcohol compound of the formula $R^{10}$—OH, wherein $R^{10}$ is an alkyl group under standard conditions, to produce a compound of the Formula XIX

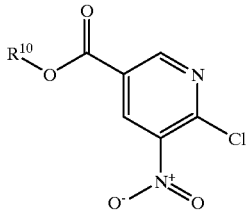

XIX (b) reacting a compound of the Formula XI wherein $R^{10}$ is an alkyl group, with ammonia in an inert solvent under standard conditions to produce a compound of the Formula XII

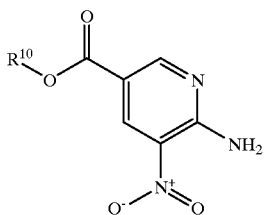

XII (c) reducing a compound of the Formula XII wherein $R^{10}$ is an alkyl group in an inert solvent under standard conditions to produce a compound of the Formula XIII

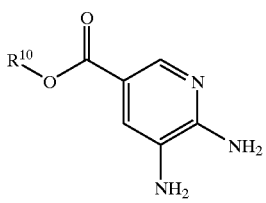

XIII (d) reacting a compound of the Formula XIII wherein $R^{10}$ is an alkyl group with a compound of Formula XIV

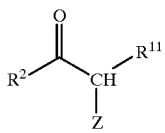

XIV wherein $R^2$ is as defined in claim 1, Z is a leaving group and $R^{11}$ represents H or $CH_3$, in an inert solvent with or without a base to produce a compound of the Formula XV

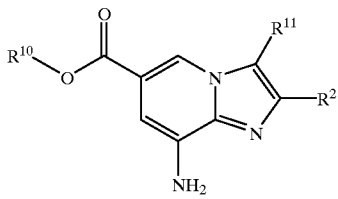

XV (e) reacting a compound of the Formula XV wherein $R^{10}$ is an alkyl group, $R^2$ is as defined in claim 1 and $R^{11}$ is H or $CH_3$ with a compound of Formula XI

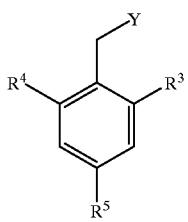

XI wherein $R^3$, $R^4$, and $R^5$ are as defined in claim 1 and Y is a leaving group in an inert solvent with or without a base to produce a compound of the Formula XVI

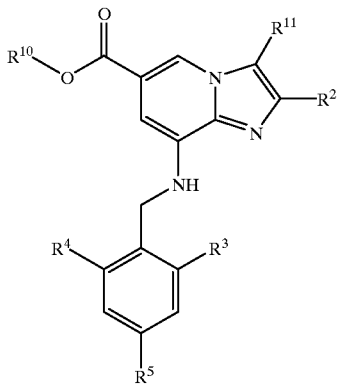

XVI (f) reacting a compound of Formula XVI wherein $R^2$, $R^3$, $R^4$ and $R^5$ are as defined in claim 1, $R^{10}$ is an alkyl group and $R^{11}$ is H or $CH_3$ with a compound of Formula IV

IV

wherein $R^6$ and $R^7$ are as defined in claim 1, under standard conditions, to produce a compound of Formula I wherein $R^1$ is H or $CH_3$ and X is NH.

9. A process for the preparation of a compound according to any one of claims 1 to 3 comprising (a) treating a compound of Formula XVII

XVII

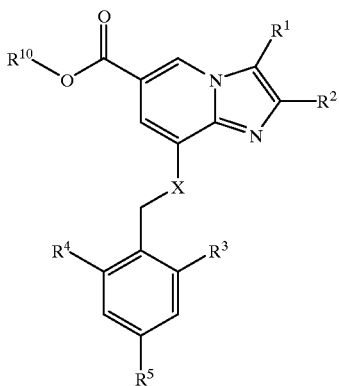

wherein $R^1$, $R^2$, $R^3$, $R^4$, $R^5$ and X are as defined in claim 1 and $R^{10}$ is an alkyl group, with acid or base under standard conditions to produce a compound of Formula III

III

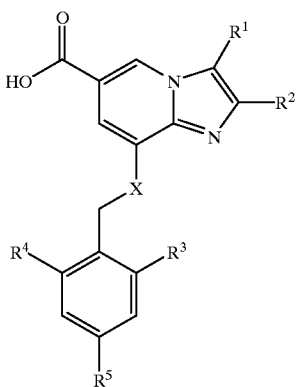

(b) reacting a compound of Formula III wherein $R^1$, $R^2$, $R^3$, $R^4$, $R^5$ and X are as defined in claim 1 with a compound of Formula IV

IV

wherein $R^6$ and $R^7$ are as defined in claim 1, in the presence of a coupling reagent in an inert solvent under standard conditions, to produce a compound of Formula I.

10. A pharmaceutical formulation containing a compound or salt thereof according to any one of claims 1 to 3 as active ingredient in combination with a pharmaceutically acceptable diluent or carrier.

11. A method for inhibiting gastric acid secretion which comprises administering to a mammal in need of such inhibition an effective amount of a compound or salt thereof according to any one of claims 1 to 3.

12. A method for the treatment of gastrointestinal inflammatory diseases which comprises administering to a mammal in need of such treatment an effective amount of a compound or salt thereof according to any one of claims 1 to 3.

13. A method for the treatment or prophylaxis involving infection by *Helicobacter pylori* of human gastric mucosa, which comprises administering to a human in need of such treatment an effective amount of a compound or salt thereof as claimed in any one of claims 1 to 3, wherein the compound or salt thereof is administered in combination with at least one antimicrobial agent.

14. A pharmaceutical formulation for use in the inhibition of gastric acid secretion wherein the active ingredient is a compound or salt thereof according to any one of claims 1 to 3.

15. A pharmaceutical formulation for use in the treatment of gastrointestinal inflammatory diseases wherein the active ingredient is a compound or salt thereof according to any one of claims 1 to 3.

16. A pharmaceutical formulation for use in the treatment or prophylaxis of conditions involving infection by *Helicobacter pylori* of human gastric mucosa, wherein the active ingredient is a compound or salt thereof according to any one of claims 1 to 3 in combination for simultaneous, separate or sequential use together with least one antimicrobial agent.

17. A compound of the formula X

X

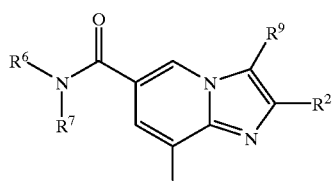

wherein $R^2$ is $CH_3$ or $CH_2CH_3$; $R^6$ and $R^7$ are independently selected substituents, comprising C, H, N, O, S, Se, P or Halogen atoms, which give compounds of Formula I

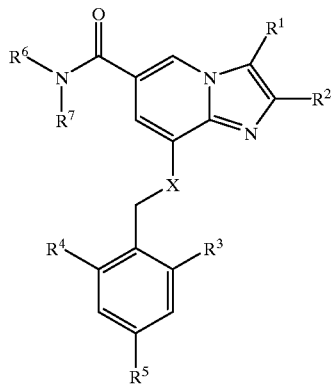

a molecular weight ≦600, provided that at least one of $R^6$ and $R^7$ can not be H, $C_1$–$C_6$ alkyl, hydroxylated $C_1$–$C_6$ alkyl, or $C_1$–$C_6$ alkoxy-substituted $C_1$–$C_6$ alkyl; and $R^9$ is H, $CH_3$ or an ester group.

18. A compound of the formula XII

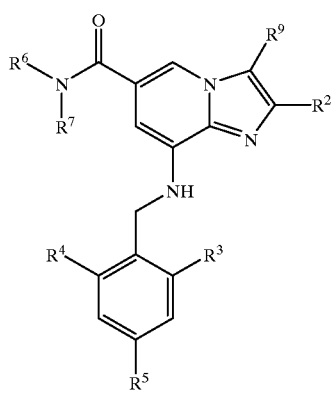

wherein $R^2$ is $CH_3$ or $CH_2CH_3$; $R^3$ is H, $C_1$–$C_6$ alkyl, hydroxylated $C_1$–$C_6$ alkyl or halogen; $R^4$ is H, $C_1$–$C_6$ alkyl, hydroxylated $C_1$–$C_6$ alkyl or halogen; $R^5$ is H or halogen; $R^6$ and $R^7$ are independently selected substituents, comprising C, H, N, O, S, Se, P or Halogen atoms, which give compounds of Formula I

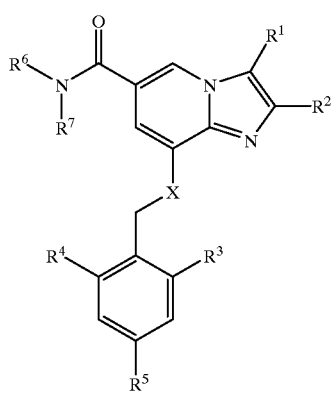

a molecular weight ≦600, provided that at least one of $R^6$ and $R^7$ can not be H, $C_1$–$C_6$ alkyl, hydroxylated $C_1$–$C_6$ alkyl, or $C_1$–$C_6$ alkoxy-substituted $C_1$–$C_6$ alkyl; and $R^9$ is an ester group.

19. A compound of the formula III

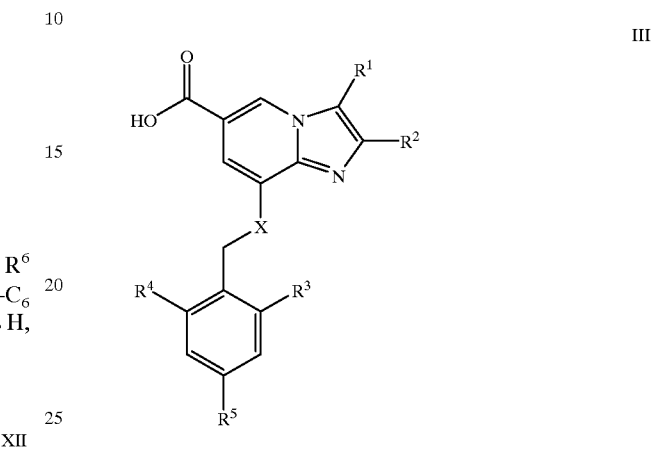

wherein $R^1$ is H, $CH_3$ or $CH_2OH$; $R^2$ is $CH_3$ or $CH_2CH_3$; $R^3$ is H, $C_1$–$C_6$ alkyl, hydroxylated $C_1$–$C_6$ alkyl or halogen; $R^4$ is H, $C_1$–$C_6$ alkyl, hydroxylated $C_1$–$C_6$ alkyl or halogen; $R^5$ is H or halogen; and X is NH or O.

20. A process for the preparation of a compound according to any one of claims 1–3, comprising (a) hydrolyzing a compound of Formula II

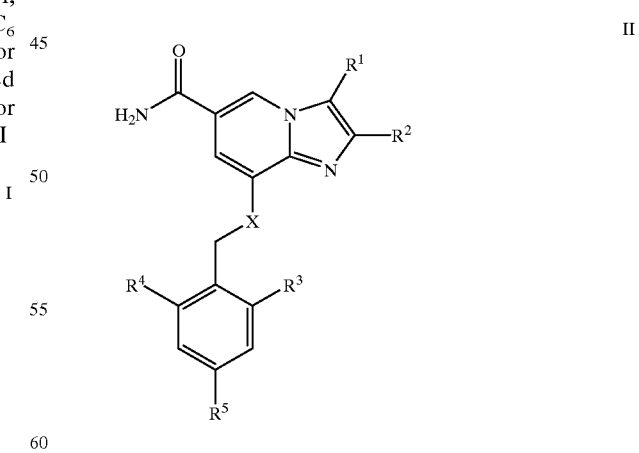

wherein $R^1$, $R^2$, $R^3$, $R^4$, $R^5$ and X are as defined in claim 1, under standard conditions to produce the corresponding carboxylic acid compound of Formula III

III

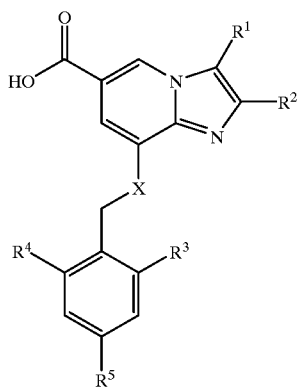

(b) reacting a compound of Formula III with an amino compound of Formula IV

IV

wherein $R^6$ and $R^7$ are as defined in claim 1, in the presence of a coupling reagent in an inert solvent and under standard conditions to produce the corresponding amide compound.

21. A product containing a compound or salt thereof according to claim 4 and at least one antimicrobial agent as a combined preparation for simultaneous, separate or sequential use in the prevention or treatment of gastrointestinal inflammatory diseases.

22. A product containing a compound or salt thereof according to claim 5 and at least one antimicrobial agent as a combined preparation for simultaneous, separate or sequential use in the prevention or treatment of gastrointestinal inflammatory diseases.

23. A product containing a compound or salt thereof according to claim 4 and at least one proton pump inhibitor as a combined preparation for simultaneous, separate or sequential use in the prevention or treatment of gastrointestinal inflammatory diseases.

24. A product containing a compound or salt thereof according to claim 5 and at least one proton pump inhibitor as a combined preparation for simultaneous, separate or sequential use in the prevention or treatment of gastrointestinal inflammatory diseases.

25. A process for the preparation of a compound according to claim 4, wherein X is NH and $R^1$ is H or $CH_3$, comprising (a) reacting a compound of the Formula V

V

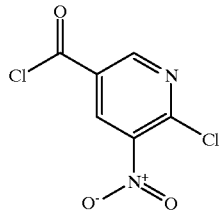

with an alcohol compound of the formula $R^{10}$—OH, wherein $R^{10}$ is an alkyl group under standard conditions, to produce a compound of the Formula XIX

XIX

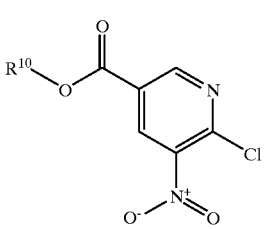

(b) reacting a compound of the Formula XI wherein $R^{10}$ is an alkyl group, with ammonia in an inert solvent under standard conditions to produce a compound of the Formula XII

XII

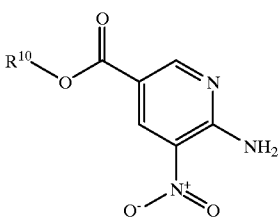

(c) reducing a compound of the Formula XII wherein $R^{10}$ is an alkyl group in an inert solvent under standard conditions to produce a compound of the Formula XIII

XIII

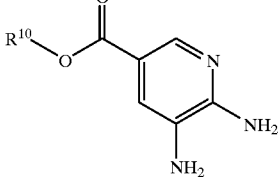

(d) reacting a compound of the Formula XIII wherein $R^{10}$ is an alkyl group with a compound of Formula XIV

XIV

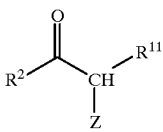

wherein $R^2$ is as defined in claim 1, Z is a leaving group and $R^{11}$ represents H or $CH_3$, in an inert solvent with or without a base to produce a compound of the Formula XV

XV

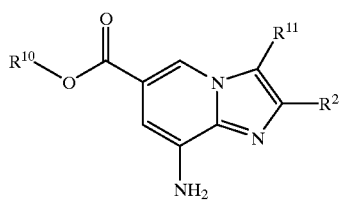

(e) reacting a compound of the Formula XV wherein $R^{10}$ is an alkyl group, $R^2$ is as defined in claim 1 and $R^{11}$ is H or $CH_3$ with a compound of Formula XI

XI

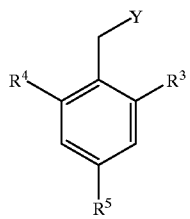

wherein $R^3$, $R^4$, and $R^5$ are as defined in claim 1 and Y is a leaving group in an inert solvent with or without a base to produce a compound of the Formula XVI

XVI

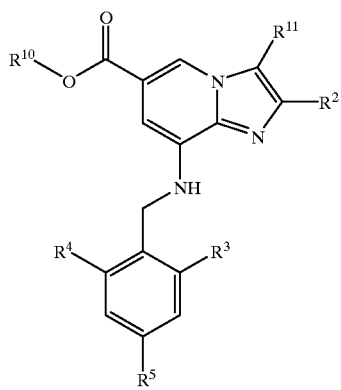

(f) reacting a compound of Formula XVI wherein $R^2$, $R^3$, $R^4$ and $R^5$ are as defined in claim 1, $R^{10}$ is an alkyl group and $R^{11}$ is H or $CH_3$ with a compound of Formula IV

IV

wherein $R^6$ and $R^7$ are as defined in claim 1, under standard conditions, to produce a compound of Formula I wherein $R^1$ is H or $CH_3$ and X is NH.

26. A process for the preparation of a compound according to claim 5, wherein X is NH and $R^1$ is H or $CH_3$, comprising (a) reacting a compound of the Formula V

V

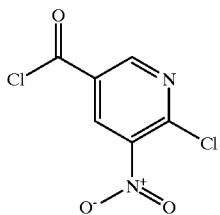

with an alcohol compound of the formula $R^{10}$—OH, wherein $R^{10}$ is an alkyl group under standard conditions, to produce a compound of the Formula XIX

XIX

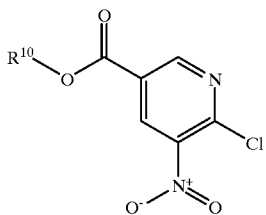

(b) reacting a compound of the Formula XI wherein $R^{10}$ is an alkyl group, with ammonia in an inert solvent under standard conditions to produce a compound of the Formula XII

XII

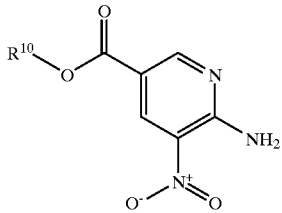

(c) reducing a compound of the Formula XII wherein $R^{10}$ is an alkyl group in an inert solvent under standard conditions to produce a compound of the Formula XIII

XIII

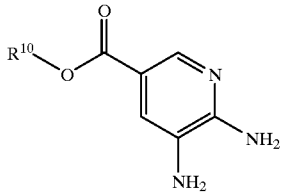

(d) reacting a compound of the Formula XIII wherein $R^{10}$ is an alkyl group with a compound of Formula XIV

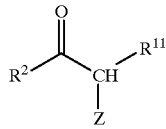
XIV wherein $R^2$ is as defined in claim 1, Z is a leaving group and $R^{11}$ represents H or $CH_3$, in an inert solvent with or without a base to produce a compound of the Formula XV

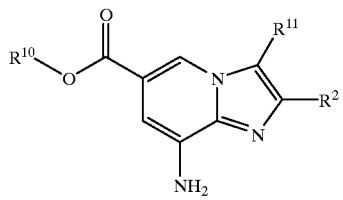
XV (e) reacting a compound of the Formula XV wherein $R^{10}$ is an alkyl group, $R^2$ is as defined in claim 1 and $R^{11}$ is H or $CH_3$ with a compound of Formula XI

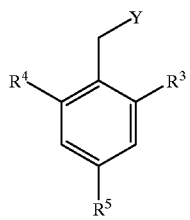
XI wherein $R^3$, $R^4$, and $R^5$ are as defined in claim 1 and Y is a leaving group in an inert solvent with or without a base to produce a compound of the Formula XVI

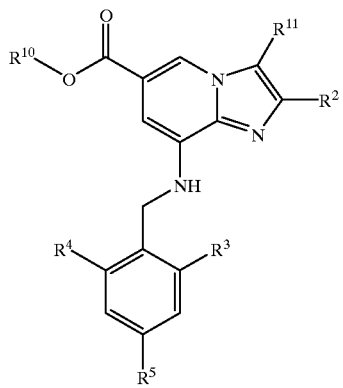
XVI (f) reacting a compound of Formula XVI wherein $R^2$, $R^3$, $R^4$ and $R^5$ are as defined in claim 1, $R^{10}$ is an alkyl group and $R^{11}$ is H or $CH_3$ with a compound of Formula IV

IV wherein $R^6$ and $R^7$ are as defined in claim 1, under standard conditions, to produce a compound of Formula I wherein $R^1$ is H or $CH_3$ and X is NH.

27. A process for the preparation of a compound according to claim 4 comprising
(a) treating a compound of Formula XVII

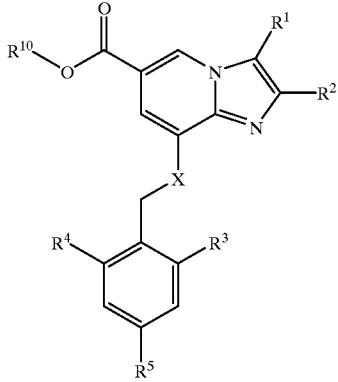
XVII wherein $R^1$, $R^2$, $R^3$, $R^4$, $R^5$ and X are as defined in claim 1 and $R^{10}$ is an alkyl group, with acid or base under standard conditions to produce a compound of Formula III

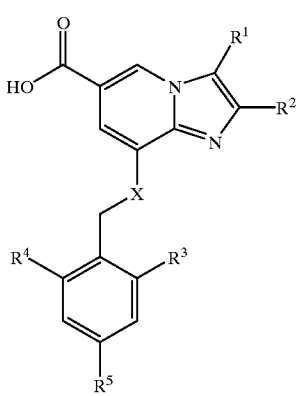
III (b) reacting a compound of Formula III wherein $R^1$, $R^2$, $R^3$, $R^4$, $R^5$ and X are as defined in claim 1 with a compound of Formula IV

IV wherein $R^6$ and $R^7$ are as defined in claim 1, in the presence of a coupling reagent in an inert solvent under standard conditions, to produce a compound of Formula I.

28. A process for the preparation of a compound according to claim 5 comprising (a) treating a compound of Formula XVII

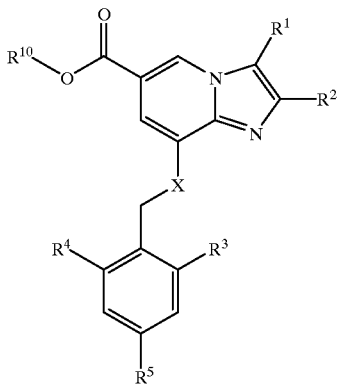

wherein $R^1$, $R^2$, $R^3$, $R^4$, $R^5$ and X are as defined in claim 1 and $R^{10}$ is an alkyl group, with acid or base under standard conditions to produce a compound of Formula III

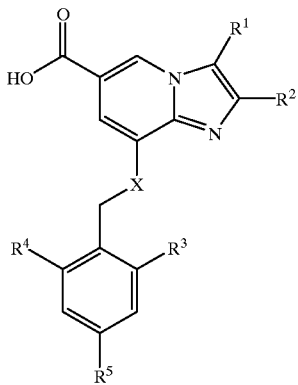

(b) reacting a compound of Formula III wherein $R^1$, $R^2$, $R^3$, $R^4$, $R^5$ and X are as defined in claim 1 with a compound of Formula IV

wherein $R^6$ and $R^7$ are as defined in claim 1, in the presence of a coupling reagent in an inert solvent under standard conditions, to produce a compound of Formula I.

29. A pharmaceutical formulation containing a compound or salt thereof according to claim 4 as active ingredient in combination with a pharmaceutically acceptable diluent or carrier.

30. A pharmaceutical formulation containing a compound or salt thereof according to claim 5 as active ingredient in combination with a pharmaceutically acceptable diluent or carrier.

31. A method for inhibiting gastric acid secretion which comprises administering to a mammal in need of such inhibition an effective amount of a compound or salt thereof according to claim 4.

32. A method for inhibiting gastric acid secretion which comprises administering to a mammal in need of such inhibition an effective amount of a compound or salt thereof according to claim 5.

33. A method for the treatment of gastrointestinal inflammatory diseases which comprises administering to a mammal in need of such treatment an effective amount of a compound or salt thereof according to claim 4.

34. A method for the treatment of gastrointestinal inflammatory diseases which comprises administering to a mammal in need of such treatment an effective amount of a compound or salt thereof according to claim 5.

35. A method for the treatment or prophylaxis involving infection by *Helicobacter pylori* of human gastric mucosa, which comprises administering to a human in need of such treatment an effective amount of a compound or salt thereof according to claim 4, wherein the compound or salt thereof is administered in combination with at least one antimicrobial agent.

36. A method for the treatment or prophylaxis involving infection by *Helicobacter pylori* of human gastric mucosa, which comprises administering to a human in need of such treatment an effective amount of a compound or salt thereof according to claim 5, wherein the compound or salt thereof is administered in combination with at least one antimicrobial agent.

37. A pharmaceutical formulation for use in the inhibition of gastric acid secretion wherein the active ingredient is a compound or salt thereof according to claim 4.

38. A pharmaceutical formulation for use in the inhibition of gastric acid secretion wherein the active ingredient is a compound or salt thereof according to claim 5.

39. A pharmaceutical formulation for use in the treatment of gastrointestinal inflammatory diseases wherein the active ingredient is a compound or salt thereof according to claim 4.

40. A pharmaceutical formulation for use in the treatment of gastrointestinal inflammatory diseases wherein the active ingredient is a compound or salt thereof according to claim 5.

41. A pharmaceutical formulation for use in the treatment or prophylaxis of conditions involving infection by *Helicobacter pylori* of human gastric mucosa, wherein the active ingredient is a compound or salt thereof according to claim 4 in combination for simultaneous, separate or sequential use together with least one antimicrobial agent.

42. A pharmaceutical formulation for use in the treatment or prophylaxis of conditions involving infection by *Helicobacter pylori* of human gastric mucosa, wherein the active ingredient is a compound or salt thereof according to claim 5 in combination for simultaneous, separate or sequential use together with least one antimicrobial agent.

43. A process for the preparation of a compound according to claim 4, comprising (a) hydrolyzing a compound of Formula II

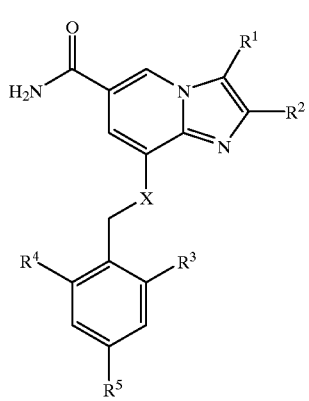

II wherein $R^1$, $R^2$, $R^3$, $R^4$, $R^5$ and X are as defined in claim 1, under standard conditions to produce the corresponding carboxylic acid compound of Formula III

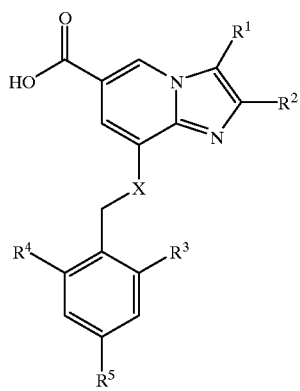

III (b) reacting a compound of Formula III with an amino compound of Formula IV

IV wherein $R^6$ and R7 are as defined in claim 1, in the presence of a coupling reagent in an inert solvent and under standard conditions to produce the corresponding amide compound.

44. A process for the preparation of a compound according to claim 5, comprising (a) hydrolyzing a compound of Formula II

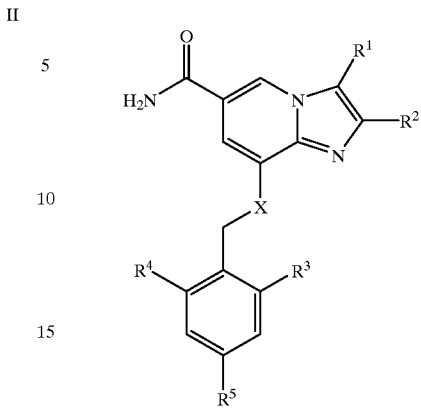

II wherein $R^1$, $R^2$, $R^3$, $R^4$, $R^5$ and X are as defined in claim 1, under standard conditions to produce the corresponding carboxylic acid compound of Formula III

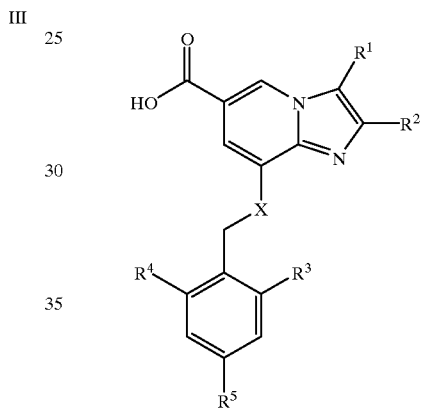

III (b) reacting a compound of Formula III with an amino compound of Formula IV

IV wherein $R^6$ and $R^7$ are as defined in claim 1, in the presence of a coupling reagent in an inert solvent and under standard conditions to produce the corresponding amide compound.

* * * * *